US011946889B2

(12) United States Patent
Monaselidze

(10) Patent No.: US 11,946,889 B2
(45) Date of Patent: Apr. 2, 2024

(54) DIFFERENTIAL SCANNING MICROCALORIMETER DEVICE FOR DETECTING DISEASE AND MONITORING THERAPEUTIC EFFICACY

(71) Applicant: Jamlet Monaselidze, Tbilisi (GE)

(72) Inventor: Jamlet Monaselidze, Tbilisi (GE)

( * ) Notice: Subject to any disclaimer, the term of this patent is extended or adjusted under 35 U.S.C. 154(b) by 0 days.

(21) Appl. No.: 17/537,913

(22) Filed: Nov. 30, 2021

(65) Prior Publication Data

US 2022/0091056 A1     Mar. 24, 2022

Related U.S. Application Data

(63) Continuation of application No. 16/070,016, filed as application No. PCT/IB2017/050197 on Jan. 13, 2017, now Pat. No. 11,215,573.

(60) Provisional application No. 62/278,458, filed on Jan. 14, 2016.

(51) Int. Cl.
    *G01K 17/00*     (2006.01)
    *G01N 25/48*     (2006.01)
    *G01N 33/483*     (2006.01)
    *G01N 33/49*     (2006.01)

(52) U.S. Cl.
CPC ....... *G01N 25/4813* (2013.01); *G01K 17/006* (2013.01); *G01N 25/4866* (2013.01); *G01N 33/483* (2013.01); *G01N 33/49* (2013.01); *G01K 17/00* (2013.01)

(58) Field of Classification Search
CPC .......... G01N 25/4813; G01N 25/4866; G01N 33/483; G01N 33/49; G01N 33/50; G01N 33/5044; G01N 33/6845; G01N 25/72; G01K 17/006; G01K 17/00; G01K 1/026; A61B 5/015; A61B 5/4312; A61B 10/0041
USPC ............................................ 422/51; 436/147
See application file for complete search history.

(56) References Cited

U.S. PATENT DOCUMENTS

| 4,368,991 A | 1/1983 | Hentze |
| 4,411,868 A | 10/1983 | Noack |
| 4,957,707 A | 9/1990 | Hofelich et al. |
| 7,252,802 B2 | 8/2007 | Bonnard |

(Continued)

FOREIGN PATENT DOCUMENTS

| AT | 000057295 T | 10/1990 | |
| CA | 3063295 A1 * | 12/2018 | ............. G01K 17/04 |

(Continued)

OTHER PUBLICATIONS

Final Office Action on U.S. Appl. No. 16/070,016 dated Sep. 14, 2020.

(Continued)

*Primary Examiner* — Gail Kaplan Verbitsky
(74) *Attorney, Agent, or Firm* — FOLEY & LARDNER LLP

(57) ABSTRACT

The present disclosure provides devices and methods for diagnosing, monitoring the disease progression of, and/or evaluating the risk for developing a disease by detecting thermostable variants of proteins and/or metabolites in biological samples using differential scanning calorimetry. Also disclosed herein are methods for monitoring the efficacy of a particular therapeutic regimen in patients in need thereof.

18 Claims, 16 Drawing Sheets

(56) References Cited

U.S. PATENT DOCUMENTS

| | | | |
|---|---|---|---|
| 7,488,106 B2* | 2/2009 | Brushwyler | G01N 25/44 |
| | | | 374/33 |
| 7,563,591 B2 | 7/2009 | Chamoles | |
| 8,926,172 B2 | 1/2015 | Wu | |
| 11,215,573 B2* | 1/2022 | Monaselidze | G01N 33/49 |
| 2002/0034210 A1 | 3/2002 | Plotnikov et al. | |
| 2006/0251145 A1* | 11/2006 | Brushwyler | G01N 25/4866 |
| | | | 374/31 |
| 2010/0093100 A1* | 4/2010 | Chaires | G01N 25/4866 |
| | | | 436/71 |
| 2011/0301860 A1* | 12/2011 | Chaires | G01N 33/54373 |
| | | | 702/19 |
| 2013/0177039 A1 | 7/2013 | Lewis et al. | |
| 2014/0113277 A1 | 4/2014 | Thomas | |
| 2014/0219311 A1 | 8/2014 | Plotnikov et al. | |
| 2014/0362888 A1* | 12/2014 | Hansen | G01K 3/14 |
| | | | 374/33 |
| 2014/0363396 A1 | 12/2014 | Waksal | |
| 2015/0079583 A1 | 3/2015 | Baudenbacher et al. | |
| 2017/0197211 A1 | 7/2017 | Kwon | |
| 2018/0116460 A1 | 5/2018 | Foser | |
| 2019/0003995 A1 | 1/2019 | Monaselidze et al. | |
| 2019/0298610 A1 | 10/2019 | Komann et al. | |
| 2019/0382826 A1 | 12/2019 | Chen et al. | |

FOREIGN PATENT DOCUMENTS

| | | | | |
|---|---|---|---|---|
| CN | 102245125 A | * | 11/2011 | ............ A61L 17/12 |
| EP | 3567596 A1 | * | 11/2019 | ............ A23K 10/30 |
| GB | 0 662 219 A | | 12/1951 | |
| JP | H0286743 A | * | 3/1990 | |
| JP | H07243167 A | * | 9/1995 | |
| WO | WO-2011156658 A2 | * | 12/2011 | ....... G01N 33/54373 |
| WO | WO-2017066800 A1 | * | 4/2017 | ............... A61B 5/00 |

OTHER PUBLICATIONS

International Search Report and Written Opinion on PCT/IB2017/050197 dated May 18, 2017.

Non-Final Office Action on U.S. Appl. No. 16/070,016 dated May 17, 2021.

Non-Final Office Action on U.S. Appl. No. 16/070,016 dated May 18, 2020.

Notice of Allowance on U.S. Appl. No. 16/070,016 dated Sep. 1, 2021.

* cited by examiner

DIFFERENTIAL SCANNING MICROCALORIMETER DEVICE FOR DETECTING DISEASE AND MONITORING THERAPEUTIC EFFICACY

CROSS-REFERENCE TO OTHER APPLICATIONS

This application is a continuation of U.S. patent application Ser. No. 16/070,016, filed on Jul. 13, 2018, which is a national phase of International Application No. PCT/IB2017/050197, filed on Jan. 13, 2017, which claims the benefit of and priority to U.S. Provisional Application No. 62/278,458, filed Jan. 14, 2016, the contents of which are incorporated herein by reference in their entireties.

TECHNICAL FIELD

The present technology relates generally to devices and methods for diagnosing, monitoring the disease progression of, and/or evaluating the risk for developing a disease by detecting thermostable variants of proteins and/or metabolites in biological samples (e.g., tissue, whole blood, plasma or serum) using differential scanning calorimetry.

BACKGROUND

There is a substantial need for sensitive and non-invasive methods that can effectively detect, and/or assess the risk for developing disease or infection in patients, even in the absence of clinical symptoms in the patients.

SUMMARY OF THE PRESENT TECHNOLOGY

According to one aspect of the disclosure, a differential scanning calorimeter (DSC) can include a furnace, at least one heater, a reference channel, and a test channel. Each of the reference channel and the test channel can extend into the furnace. Each of the reference channel and the test channel can include a conically shaped receiving end. The conically shaped receiving end can slope at a predetermined angle.

The differential scanning calorimeter can include at least one vessel. The at least one vessel can be configured to slide into each of the reference channel and the test channel and mate with the conically shaped receiving end of the respective channel. The at least one vessel can be conically shaped.

A wall of the at least one conically shaped vessel can slope at the same predetermined angle as the reference and test channel. The predetermined angle is between about 1 and about 5 degrees.

The at one vessel can be configured to hold between about 50 µL and about 250 µL. The at least one vessel can include titanium, gold, platinum, an engineered polymer, block copolymer, polymer composite, or a combination thereof. The at least one vessel can be configured to be directly filled. A wall of the reference channel and the test channel can each include titanium, copper, gold, platinum, or a combination thereof.

In one aspect, the present technology provides methods for detecting thermostable variants of proteins and/or metabolites in a biological sample (e.g., tissue, whole blood, plasma or serum) comprising: (a) loading an undiluted fraction of the biological sample into the differential scanning calorimeter of the present technology; (b) generating a signature DSC thermogram from the undiluted fraction of the biological sample; and (c) detecting thermostable variants of proteins and/or metabolites when at least one alteration is present in the signature DSC thermogram of the biological sample relative to that observed in a DSC thermogram generated from a normal control sample. The sample may be obtained from a patient that is suspected of having, or is at risk for a disease or condition. In some embodiments, the disease or condition is selected from the group consisting of: cancer (e.g., breast cancer, brain cancer, myeloma, acute myeloblastic promyelocyte leukemia, Waldenstrom's disease etc.), a pathogenic infection, diabetes mellitus, cardiovascular disease, neurodegenerative disease (e.g., Alzheimer's disease, Amyotrophic lateral sclerosis, Friedreich's ataxia, Huntington's disease, Lewy body disease, Parkinson's disease, spinal muscular atrophy etc.), and rheumatic disease. In certain embodiments, the patient is suffering from stage 0, stage I, stage II, stage III, or stage IV cancer. Additionally or alternatively, in certain embodiments, the patient lacks any detectable rigid tumor mass (e.g., in soft breast tissue, brain tissue, etc.).

In some embodiments, the rheumatic disease is selected from the group consisting of: osteoarthritis, rheumatoid arthritis, ankylosing spondylitis, Sjögren's syndrome, Antinuclear Antibodies (ANA), Antiphospholipid Syndrome, Calcium Pyrophosphate Deposition (CPPD), Carpal Tunnel Syndrome, Cryopyrin-Associated Autoinflammatory Syndrome (CAPS), Dermatomyositis, familial Mediterranean fever, fibromyalgia, giant cell arteritis, glucocorticoid-induced osteoporosis, gout, granulomatosis with Polyangitis (Wegener's), hypermobility, Hyperimmunoglobulin D Syndrome, inflammatory myopathies, juvenile arthritis, scleroderma, Lyme disease, metabolic myopathies, osteonecrosis, osteonecrosis of the jaw (ONJ), osteoporosis, Paget's disease, PFAPA (Periodic Fever, Aphthous Stomatitis, Pharyngitis, Adenitis Syndrome), polymyalgia rheumatic, psoriatic arthritis, Raynaud's phenomenon, reactive arthritis, spinal stenosis, spondyloarthritis, Systemic Lupus Erythematosus, Takayasu's arteritis, Tendinitis & bursitis, Tumor Necrosis Factor Receptor Associated Periodic Syndrome, and vasculitis.

The pathogenic infection may be bacterial, viral or fungal. In some embodiments, the pathogenic infection is caused by *Clostridium difficile*, carbapenem-resistant Enterobacteriaceae, multidrug resistant *Acinetobacter*, multidrug resistant *Campylobacter*, flucoazole resistant *Candida*, extended spectrum beta-lactamase-producing Enterobacteriaceae, Vancomycin Resistant Enterococci, Multi-drug resistant *Pseudomonas aeruginosa*, drug resistant Non-typhoidal *Salmonella*, drug resistant *Salmonella* serotype *Typhi*, drug resistant *Shigella*, Methicillin-Resistant *Staphylococcus aureus*, drug resistant *Streptococcus pneumoniae*, or drug resistant *Mycobacterium tuberculosis*. In other embodiments, the pathogenic infection is caused by hepatitis B virus, hepatitis C virus, HIV, Human Papilloma Virus, or Epstein Barr virus.

Additionally or alternatively, in some embodiments, the biological sample is plasma, serum, whole blood, or tissue (i.e., non-homogenized, unprocessed tissue). In certain embodiments, the volume of the biological sample is no more than 20 µL. In other embodiments, the volume of the biological sample is about 20-50 or about 50-125 µL.

In any of the above embodiments of the methods of the present technology, the at least one alteration present in the signature DSC thermogram of the biological sample may comprise one or more of: an increase in $\Delta T_m$ at half max (integral melting width) by at least 10%, a reduction in excess heat capacity (dQ/dT) by about 10-20%, a 5-8° C. increase in main peak $T_m$, or detection of a new shoulder or peak at 58-60° C. In certain embodiments, the concentration of proteins that melt at 56-63° C. with a maximum $T_m$ of 59±1° C. is 650±120 μg/ml, 120±50 μg/ml, or 150±60 μg/ml.

Additionally or alternatively, in some embodiments of the methods disclosed herein, the at least one alteration present in the signature DSC thermogram of the biological sample may comprise one or more of: detection of new shoulders or peaks at 69° C. and 75° C., an increase in the integral melting width of the dual peak by at least 200%, and a reduction in excess heat capacity (dQ/dT) by about 50%.

Additionally or alternatively, in some embodiments of the methods disclosed herein, the at least one alteration present in the signature DSC thermogram of the biological sample may comprise one or more of: detection of a new peak at 70° C., 75° C., and/or 80.7-83.3° C.; detection of a sharp peak at 70±1.0° C.; an increase in Y-Globulin concentration by at least 400%; an increase in ΔC excess (dQ/dT) of Y-Globulin by about 400%; an increase in main peak width by at least 250%; and a 20-35% decrease in ΔC excess of albumin.

Additionally or alternatively, in some embodiments of the methods disclosed herein, the at least one alteration present in the signature DSC thermogram of the biological sample may comprise one or more of: detection of a new peak at 57±1.3° C., an increase in Bence Jones protein concentration by at least 200%, and a reduction of albumin concentration by about 15-20%.

Additionally or alternatively, in some embodiments of the methods disclosed herein, the at least one alteration present in the signature DSC thermogram of the biological sample may comprise detection of a new peak or shoulder at 62° C., 66° C. and/or 85° C.

Additionally or alternatively, in some embodiments of the methods disclosed herein, the at least one alteration present in the signature DSC thermogram of the biological sample may comprise detection of a power peak at 66° C.

Additionally or alternatively, in some embodiments of the methods disclosed herein, the at least one alteration present in the signature DSC thermogram of the biological sample may comprise detection of a new peak or shoulder at 55° C., 67° C., and/or 85.5° C.

In another aspect, the present disclosure provides a method for identifying a subject as having, or at risk for cancer comprising (a) loading an undiluted fraction of a biological sample obtained from the subject into the differential scanning calorimeter disclosed herein; (b) generating a signature DSC thermogram from the undiluted fraction of the biological sample; and (c) identifying the subject as having, or at risk for cancer when at least one alteration is present in the signature DSC thermogram of the biological sample relative to that observed in a DSC thermogram generated from a normal control sample. The biological sample may be plasma, serum, whole blood, or tissue (i.e., non-homogenized, unprocessed tissue). In some embodiments, the cancer is breast cancer, brain cancer, acute myeloblastic promyelocyte leukemia, Waldenstrom's disease, multiple myeloma G, multiple myeloma A, or Bence Jones myeloma.

In some embodiments of the method, the at least one alteration present in the signature DSC thermogram of the biological sample may comprise one or more of: an increase in $\Delta T_m$ at half max (integral melting width) by at least 10%, a reduction in excess heat capacity (dQ/dT) by about 10-20%, a 3-8° C. increase in main peak $T_m$, or detection of a new shoulder or peak at 58-60° C. In a further embodiment, the concentration of proteins that melt at 56-63° C. with a maximum $T_m$ of 59±1° C. is 650±120 μg/ml, 120±50 μg/ml, or 150±60 μg/ml.

In certain embodiments of the method, the at least one alteration present in the signature DSC thermogram of the biological sample may comprise one or more of: detection of new shoulders or peaks at 69° C. and 75° C., an increase in the integral melting width of the dual peak by at least 200%, and a reduction in excess heat capacity (dQ/dT) by about 50%.

In other embodiments of the method, the at least one alteration present in the signature DSC thermogram of the biological sample may comprise one or more of: detection of a new peak at 70° C., 75° C., and/or 80.7-83.3° C.; detection of a sharp peak at 70±1.0° C.; an increase in Y-Globulin concentration by at least 400%; an increase in ΔC excess (dQ/dT) of Y-Globulin by about 400%; an increase in main peak width by at least 250%; and a 20-35% decrease in ΔC excess of albumin.

In some embodiments of the method, the at least one alteration present in the signature DSC thermogram of the biological sample may comprise one or more of: detection of a new peak at 57±1.3° C., an increase in Bence Jones protein concentration by at least 200%, and a reduction of albumin concentration by about 15-20%.

In some embodiments of the method, the at least one alteration present in the signature DSC thermogram of the biological sample may comprise detection of a new peak or shoulder at 62° C., 66° C. and/or 85° C.

In certain embodiments of the method, the at least one alteration present in the signature DSC thermogram of the biological sample may comprise detection of a power peak at 66° C.

Additionally or alternatively, in some embodiments of the method, the subject does not exhibit any detectable rigid tumor mass.

Additionally or alternatively, in some embodiments, the method further comprises administering to the subject an effective amount of radiation therapy, hormonal therapy, chemotherapy, immunotherapy, surgery, or combinations thereof.

In another aspect, the present disclosure provides a method for diagnosing a subject as having a pathogenic infection comprising (a) loading an undiluted fraction of a biological sample obtained from the subject into the differential scanning calorimeter disclosed herein; (b) generating a signature DSC thermogram from the undiluted fraction of the biological sample; and (c) diagnosing the subject with a pathogenic infection when at least one alteration is present in the signature DSC thermogram of the biological sample relative to that observed in a DSC thermogram generated from a normal control sample. The pathogenic infection may be bacterial, fungal, or viral. In some embodiments, the pathogenic infection is caused by *Clostridium difficile*, carbapenem-resistant Enterobacteriaceae, multidrug resistant *Acinetobacter*, multidrug resistant *Campylobacter*, flucoazole resistant *Candida*, extended spectrum beta-lactamase-producing Enterobacteriaceae, Vancomycin Resistant Enterococci, Multi-drug resistant *Pseudomonas aeruginosa*, drug resistant Non-typhoidal *Salmonella*, drug resistant *Salmonella* serotype *Typhi*, drug resistant *Shigella*, Methicillin-Resistant *Staphylococcus aureus*, drug resistant *Streptococcus pneumoniae*, or drug resistant *Mycobacterium tuberculosis*. In other embodiments, the pathogenic infection is caused by hepatitis B virus, hepatitis C virus, HIV, Human Papilloma Virus, or Epstein Barr virus.

In some embodiments, the at least one alteration present in the signature DSC thermogram of the biological sample comprises one or more of: detection of a double peak at 67° C. and 70° C., an increase in $\Delta T_m$ at half max (integral melting width) by at least 100%, a reduction in excess heat capacity (dQ/dT) by 12-45% and 22-60% for peaks 67° C. and 70° C. compared to dQ/dT of Albumin; and detection of a new weak shoulder at 84° C.

In some embodiments, the at least one alteration present in the signature DSC thermogram of the biological sample comprises detection of a new peak or shoulder at 55° C., 67° C., and/or 85.5° C.

In some embodiments, the method further comprises administering to the subject an effective amount of one or more of interferon alfacon-1, pegylated and/or non-pegylated interferon alfa-2b, peginterferon alfa-2a, ribavirin, telaprevir, boceprevir, sofosbuvir, simeprevir, daclatasvir, velpatasvir, ombitasvir, paritaprevir, ritonavir, dasabuvir, ledipasvir, elbasvir, danoprevir, grazoprevir, GS-7977, β-interferon, γ-interferon, amantadine, or 3TC.

In any of the above embodiments of the methods, the biological sample is plasma, serum, whole blood, or tissue. In some embodiments, the volume of the biological sample is about 50-125 µL, about 20-50 µL, or no more than 20 µL.

In one aspect, the present disclosure provides a method for detecting the onset of relapse in a patient diagnosed as having a disease or condition comprising: (a) loading an undiluted fraction of a biological sample obtained from the patient into the differential scanning calorimeter disclosed herein; (b) generating a signature DSC thermogram from the undiluted fraction of the biological sample; and (c) detecting the onset of relapse in the patient when at least one alteration is present in the signature DSC thermogram of the biological sample relative to that observed in a DSC thermogram generated from a normal control sample, wherein the at least one alteration is similar or identical to that observed in a DSC thermogram generated from a positive control sample having the disease or condition. The disease or condition may be breast cancer, brain cancer, myeloma, acute myeloblastic promyelocyte leukemia, Waldenstrom's disease, a pathogenic infection, or any other disease or condition described herein. Additionally or alternatively, in some embodiments, the method further comprises monitoring the progression of the disease or condition using the differential scanning calorimeter of the present technology.

In another aspect, the present disclosure provides a method for evaluating the efficacy of a therapeutic regimen in a patient in need thereof comprising (a) loading an undiluted fraction of a biological sample obtained from the patient following administration of the therapeutic regimen into the differential scanning calorimeter disclosed herein; (b) generating a signature DSC thermogram from the undiluted fraction of the biological sample; and (c) determining the therapeutic regimen is efficacious when the signature DSC thermogram of the biological sample resembles a DSC thermogram generated from a normal control sample. In some embodiments, the patient is diagnosed with, or is at risk for a disease or condition selected from among breast cancer, brain cancer, myeloma, acute myeloblastic promyelocyte leukemia, Waldenstrom's disease, a pathogenic infection, or any disease or condition described herein. Additionally or alternatively, in some embodiments, the signature DSC thermogram of the biological sample shows at least one alteration relative to that observed in a DSC thermogram generated from a sample obtained from the patient prior to administration of the therapeutic regimen. Additionally or alternatively, in some embodiments, the method further comprises monitoring the efficacy of the therapeutic regimen using the differential scanning calorimeter of the present technology.

BRIEF DESCRIPTION OF THE DRAWINGS

FIG. 6(a) shows deconvolution of blood plasma curves for a 62 year old woman with stage II breast cancer. FIG. 6(b) shows deconvolution of blood plasma curves for the same 62 year old woman (shown in FIG. 6(a)) at 14 years post-surgery (stage IV breast cancer). FIG. 6(c) shows deconvolution of blood plasma curves for a 40 year old daughter of the same patient shown in FIGS. 6(a) and (b), demonstrating that the daughter is at risk for developing breast cancer. FIG. 6(d) shows deconvolution of blood plasma curves for a healthy 32 year old woman. FIG. 6(e) shows deconvolution of blood plasma curves for a 55 year old woman with stage III breast cancer.

DETAILED DESCRIPTION

Figure 1:
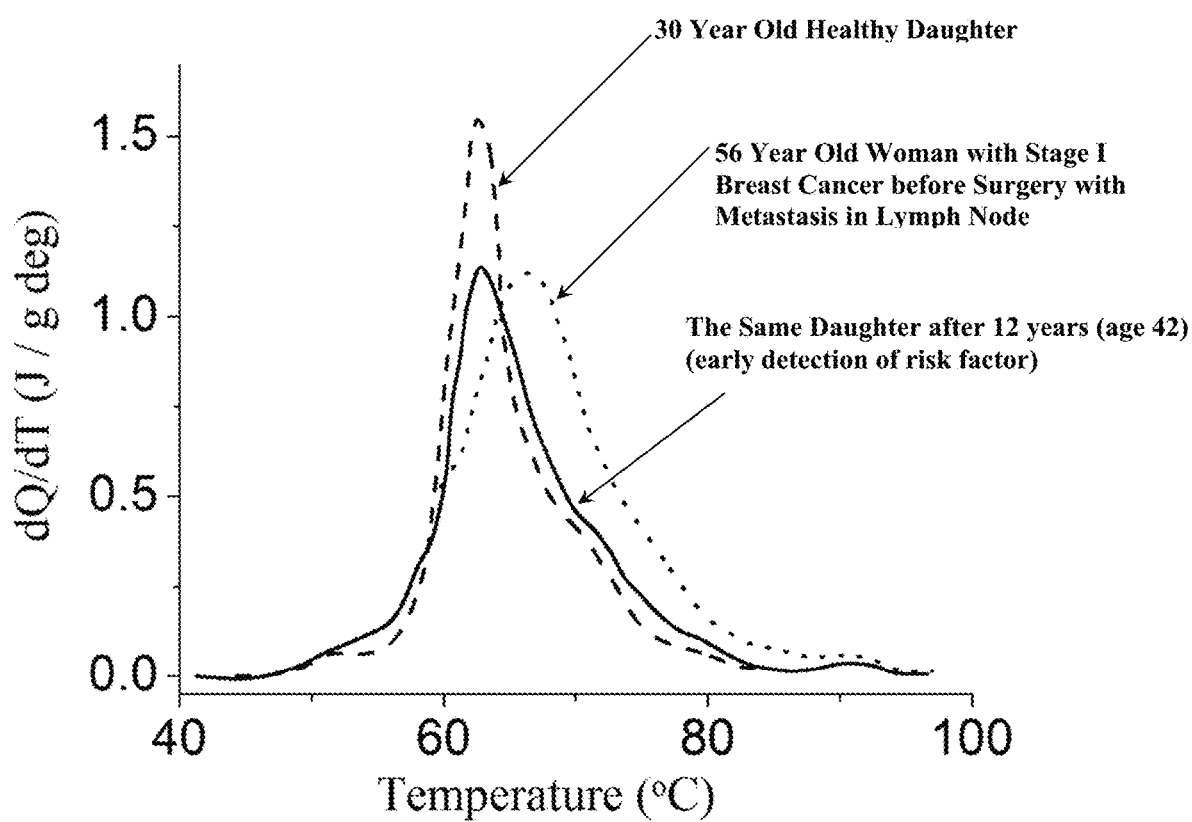
FIG. 1 shows heat absorption curves (heat capacity dQ/dT, J $g^{-1°}$ $C.^{-1}$) as a function of temperature of blood plasma samples obtained from a 56 year old woman and her daughter, recalculated per gram dry biomass: Dash line: 30 year old healthy daughter; Solid line: the same daughter after 12 years (age 42); Dot line: 56 year old mother with breast cancer before surgery with metastasis in lymph node (stage I breast cancer).

The present disclosure discusses a differential scanning calorimeter and methods of using the differential scanning calorimeter. The differential scanning calorimeter includes a number of advantages over present devices. For example, the test and reference channels of the differential scanning calorimeter can be configured to have a conically shaped receiving end. The vessels configured for use with the differential scanning calorimeter can also be conically shaped and mate with the conically shaped end of the test and reference channels. The conical shape of the channels and vessels can provide greater consistence in scanning results and greater accuracy. The conical shape can enable the vessel to intimately contact (e.g., substantially no gap exists) the wall of the channel throughout a scan. Thermal expansion of the materials requires that a gap initially be left between a cylindrical vessel and cylindrical channel wall. However, when the vessel and channel are conically shaped, the vessel and channel can be in intimate contact throughout the scan because an initial gap between the vessel and channel is not needed. Thermal expansion of the vessel causes the vessel to slide up along the wall of the conical channel, but remains in intimate contact throughout the scan. The vessels of the present disclosure are also directly filled and then hermetically sealed. When the vessels are directly filled, the vessel is removed from the differential scanning calorimeter, opened, filled by the user, sealed, and placed into the differential scanning calorimeter. Direct filling of the vessel means that the vessel is not filled via tubing, which can clog. This enables smaller, undiluted samples to be tested.

The methods of the present technology permit early detection of a disease or a condition in a subject, and/or identification of subjects at risk for a disease or a condition based on the thermodynamic stability of biomarkers, metabolites, proteins, lipids, saccharides, etc., and their influence on the structure and/or content of proteins present in tissue, whole blood, plasma or serum in patients. The DSC methods of the present technology can effectively detect thermostable variants of proteins and/or metabolites present in small volume (e.g., 50-125 μL) undiluted biological samples (e.g., serum, plasma, whole blood or solid tissue) in about ~20-120 minutes. The methods of the present technology comprise scanning plasma/serum proteins at different temperatures up to full denaturation, and rendering a diagnosis based on the appearance of new peaks or shoulders in the DSC curve and/or the increased $T_m$ or $\Delta T_m$ of protein fractions, such as major albumin fraction. The methods disclosed herein assess the $T_m$, $\Delta T_m$, $\Delta H_m$ and $DC^{max}$ values of major plasma proteins, and quantify suspected biomarkers, metabolites, proteins, lipids, saccharides, etc. via deconvolution analyses of the DSC curves, allowing one to discriminate between disease states and healthy controls.

The methods disclosed herein are non-invasive, cost-effective, and can rapidly detect cancer with high sensitivity and specificity, even when little to no rigid tumor mass is detected in patient tissue using conventional image-based screening methods. Unlike X-ray imaging, the methods of the present technology may be repeatedly used in vulnerable patient populations, particularly young and pregnant women, or cancer patients who are recovering from surgery. The methods disclosed herein are also useful for detecting an infection in a patient, even when a pathogen is present at low concentrations in a patient. The methods of the present technology are also useful for monitoring disease progression (e.g., onset of relapse) and/or the efficacy of a particular therapeutic regimen in patients in need thereof.

Definitions

As used herein, the term "about" in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

As used herein, the "administration" of an agent, drug, or compound to a subject includes any route of introducing or delivering to a subject a compound to perform its intended function. Administration can be carried out by any suitable route, including orally, intranasally, intrathecally, parenterally (intravenously, intramuscularly, intraperitoneally, or subcutaneously), topically, transdermally, or any other route known in the art. Administration includes self-administration and the administration by another.

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease, a positive control (a compound or composition known to exhibit the desired therapeutic effect) and a negative control (a subject or a sample that does not receive the therapy or receives a placebo) are typically employed.

As used herein, the term "effective amount" refers to a quantity sufficient to achieve a desired therapeutic and/or prophylactic effect, e.g., an amount which results in the prevention of, or a decrease in a disease or condition described herein or one or more signs or symptoms associated with a disease or condition described herein. In the context of therapeutic or prophylactic applications, the amount of a composition administered to the subject will vary depending on the composition, the degree, type, and severity of the disease and on the characteristics of the individual, such as general health, age, sex, body weight and tolerance to drugs. The skilled artisan will be able to determine appropriate dosages depending on these and other factors. The compositions can also be administered in combination with one or more additional therapeutic compounds. In the methods described herein, the therapeutic compositions may be administered to a subject having one or more signs or symptoms of a disease or condition described herein. As used herein, a "therapeutically effective amount" of a composition refers to composition levels in which the physiological effects of a disease or condition are ameliorated or eliminated. A therapeutically effective amount can be given in one or more administrations.

As used herein, the terms "individual", "patient", or "subject" can be an individual organism, a vertebrate, a mammal, or a human. In certain embodiments, the individual, patient or subject is a human.

As used herein, the term "sample" refers to clinical samples obtained from a patient. In some embodiments, a sample is obtained from a biological source (i.e., a "biological sample"), such as tissue, or bodily fluid collected from a subject. Sample sources include, but are not limited to, stool, mucus, sputum (processed or unprocessed), bronchial alveolar lavage (BAL), bronchial wash (BW), blood, bodily fluids, cerebrospinal fluid (CSF), urine, plasma, serum, or tissue (e.g., biopsy material). In certain embodiments, the sample comprises one or more of plasma, serum or whole blood.

"Treating" or "treatment" as used herein covers the treatment of a disease or condition (e.g., breast cancer) in a subject, such as a human, and includes: (i) inhibiting a disease or condition, i.e., arresting its development; (ii) relieving a disease or condition, i.e., causing regression of the disease or condition; (iii) slowing progression of the disease or condition; and/or (iv) inhibiting, relieving, or slowing progression of one or more symptoms of the disease or condition.

It is also to be appreciated that the various modes of treatment of the diseases or conditions described herein are intended to mean "substantial," which includes total but also less than total treatment, and wherein some biologically or medically relevant result is achieved. The treatment may be a continuous prolonged treatment for a chronic disease or a single, or few time administrations for the treatment of an acute condition.

DSC Devices of the Present Technology

In conventional capillary-based DSC methods, blood and serum samples are generally dissolved, sometimes by about 24-fold, to prevent gelling and/or clogging of the samples within the capillaries. As demonstrated in Example 2, dilution of biological samples can reduce the accuracy of the thermostability profiles of serum/plasma proteins and requires higher sample volume and more time to complete the analysis of a sample. Unlike conventional capillary-based DSC devices, the device of the present technology can rapidly and effectively process and analyze undiluted biological samples, thereby providing an accurate reflection of the actual thermostability profiles of the plasma/serum proteins in vivo.

Figure 8A:
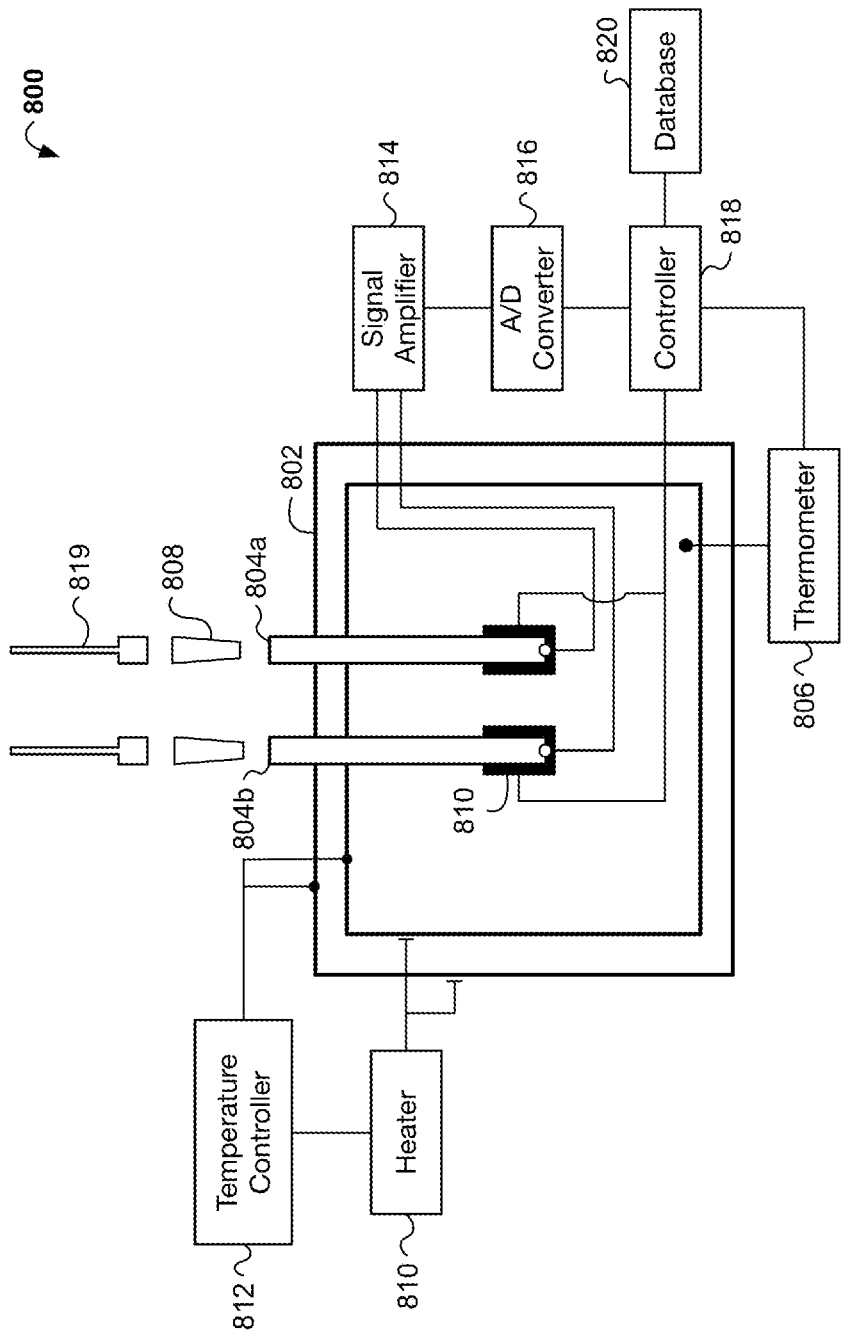
FIG. 8(a) illustrates a schematic of exemplary embodiments of the differential scanning calorimeter of the present technology.

FIG. 8(a) illustrates an example differential scanning calorimeter 800. The differential scanning calorimeter 800 includes a furnace 802. The differential scanning calorimeter 800 includes a reference channel 804a and a test channel 804b (collectively referred to as channels 804). Separate vessels 808 can be loaded into each of the channels 804. The channels 804 can be sealed with channel sealers 819 that press the vessel 808 toward the receiving end of each of the channels 804. The differential scanning calorimeter 800 includes a heater 810 that heats the furnace 802. The differential scanning calorimeter 800 also includes a temperature controller 812 that controls the output of the heater 810. The signal amplifier 814 receives a signal from thermocouples coupled to each of the test and reference channels 804. The signal generated by the signal amplifier 814 is output to an analog to digital (A/D) converter 816, which is supplied to a controller 818. The controller can also measure the temperature in the furnace 802 with a thermometer 806. The controller 818 can also reference a database 820.

Figure 8B:
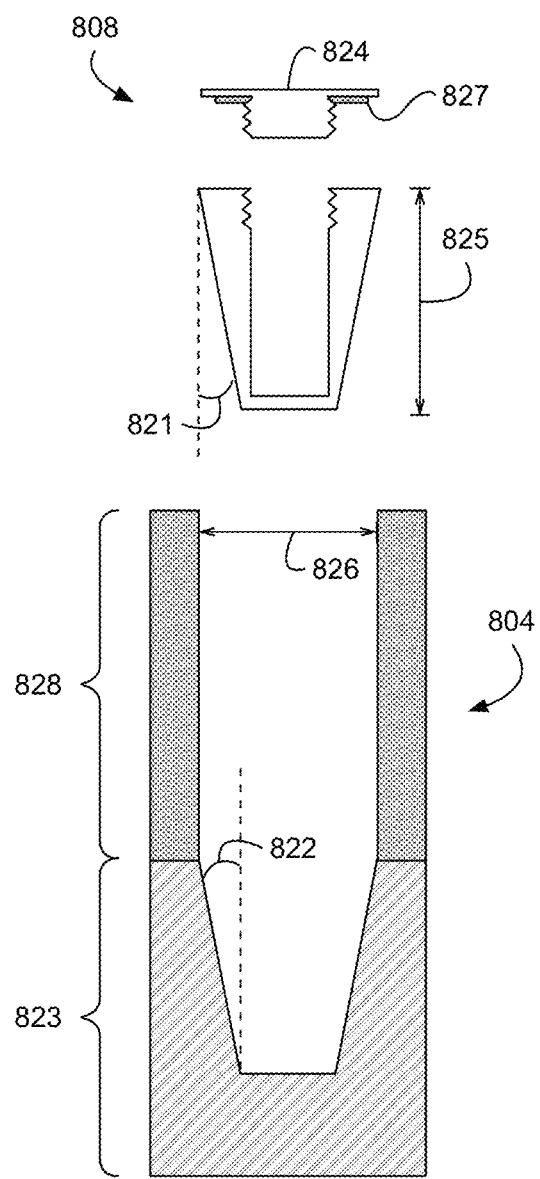
FIG. 8(b) illustrates an exemplary vessel that can be used with the differential scanning calorimeter illustrated in FIG. 8(a).

The vessels 808 and channels 804 are described further in relation to FIG. 8(b). As an overview, the vessel 808 can be a hermetically sealed vessel. A user of the differential scanning calorimeter 800 can directly load a sample into the vessel 808, which can then be loaded into the test channel 804b. A reference material can be directly loaded into the vessel 808 that is loaded into the reference channel 804a. The vessels 808 can be directly filled by a user and loaded directly into the furnace, rather than being loaded once in the furnace by a user via capillary or other tubing. This can have a number of advantages. First, the tubing can often become clogged with the sample. For example, if the sample is blood, the blood can coagulate and clog the tubing leading to the vessel 808. To prevent coagulation and clogging of the tubes, the samples can be diluted, which can impair the accuracy of the differential scanning calorimeter. In implementations where the vessel 808 is directly filled, the sample does not need to be diluted. This can provide more accurate results when compared to systems with vessels that are filled via tubing. A second benefit is that a system without tubing can be easier to use. For example, the tubing used to load the vessels must be cleaned or replaced between runs. The present system, without tubing to load the vessels is easier to operate because tubing does not need to be replaced or cleaned between uses. Not having to replace or clean tubing between scans enables a user to perform a greater number of scans over a given period of time.

The differential scanning calorimeter 800 also includes a channel sealer 819 for each channel 804. The channel sealer 819 can seal the respective channel 804 and keep the vessel 808 pressed against the receiving end of the channel 804.

The differential scanning calorimeter 800 also includes the heater 810. The heater 810 can heat the furnace in multiple locations. For example, the furnace can include multiple interior walls, and the heater 810 can apply heat to each of the walls of the furnace. The differential scanning calorimeter 800 can also include heaters 810 coupled near the receiving end of each of the channels 804. The individual heaters 810 can individually heat each of the channels 804. The heater 810 can be controlled by the temperature controller 812. The heaters 810 coupled to the channels 804 can be controlled by the controller 818. The controllers 812 and 818 can receive input from thermocouples positioned at locations throughout the furnace. In some implementations, the controller 810 can control the heaters 810 such that heaters 810 heat each of the vessels 808 to a temperature between about 50° C. and about 200° C., between about 75° C. and about 150° C., or between about 100° C. and about 150° C. The heater 810 can increase the temperature of the vessels 808 between about 1° C. and about 10° C., about 1° C. and about 8° C., or about 1° C. and about 5° C. per minute.

The differential scanning calorimeter 800 can also include one or more thermocouples to measure the temperature of each of the channels 804. The thermocouples include dissimilar metal conductors and can be coupled to or embedded within a wall of the channels 804. The thermocouples generate a temperature dependent voltage at the junction of the conductors. The voltages generated by the thermocouples can be supplied to a signal amplifier 814, which can have a threshold sensitivity of at least 0.1 μV and can have an amplification coefficient of at least 30,000. In some implementations, the differential scanning calorimeter 800 includes a thermal battery between the two channels 804. The signal amplifier 814 can amplify the output of the thermal battery. The thermal battery can include a plurality of thermocouples coupled with the walls of both channels. The thermal battery can include between 50 and about 200 or between about 50 and 100 thermocouples. The thermocouples can be chromel-constantan thermocouples. The A/D converter 816 can then convert the analog signal from the signal amplifier 814 into a digital signal, which the A/D converter 816 supplies to the controller 818. The A/D converter 816 can be an 8, 12, 16, or 32 bit A/D converter. In some implementations, the A/D converter 816 is a component of the controller. For example, the controller 818 can be a microprocessor and the signal amplifier 814 can be coupled with the microprocessor that includes an A/D converter.

The controller 818 can include one or more processors. The processors can execute one or more computer programs to perform actions such a measuring the temperatures of the channels 804, controlling the heater 810, and calculating differential scanning calorimetry measurements. In some implementations, the controller 818 can be implemented as special purpose logic circuitry, e.g., an FPGA (field programmable gate array) or an ASIC (application-specific integrated circuit). The controller can include one or more memory devices that are suitable for storing computer executable instructions and data. The database 820 can include all forms of non-volatile memory, media and memory devices, including, but not limited to, flash memory devices, magnetic disks, internal hard disks or removable disks, optical disks, and network attached storage.

FIG. 8(*b*) illustrates a cross section of an example vessel 808 positioned above a channel 804. The vessel 808 can be hermetically sealed with a cap 824. The height 825 of the vessel 808 is between about 10 mm and about 30 mm, between about 10 mm and about 25 mm, or between about 15 mm and about 20 mm. The outer diameter of the vessel 808 and the inner diameter 826 of channel can between about 5 mm and about 20 mm, between about 5 mm and about 15 mm, or between about 5 mm and about 10 mm. The inner diameter of the vessel 808 can be between about 2 mm and about 10 mm, between about 2 mm and about 7.5 mm, or between about 2 mm and about 5 mm. The dimensions of the vessel 808 can be configured such that the vessel 808 holds between about 50 μL and about 500 μL, between about 50 μL and about 400 μL, between about 50 μL and about 250 μL, or between about 50 μL and about 100 μL.

In some implementations, the vessel 808 is reusable, and in other implementations the vessel 808 is disposable. The vessel 808 can include copper, titanium, gold, platinum, or a combination thereof. In some implementations, the interior wall of the vessel 808 can be coated in gold. The materials used to construct the vessel 808 are selected to be inert to the sample placed in the vessel 808. The vessel 808 can include a polymer with high thermal conductivity, such as polycarbonate, engineered polymer, block copolymer or polymer composite, e.g., Teflon. The channel 804 can include copper, titanium, gold, platinum, or a combination thereof. The channel 804 can include multiple sections. A receiving end 823, where the vessel 808 mates with the channel 804 can include a material with a high thermal conductivity and low heat capacity, such as copper. An upper end 828, leading to the receiving end 823, can include a material with a relatively low thermal conductivity, such as stainless steel. The upper end 828 can include a material with a thermal conductivity lower than that of the receiving end 823 to keep thermal energy within the receiving end 823 and to hinder the spread of the thermal energy along the length of the channel 804.

The upper end 828 of the channel 804 can have relatively thin walls compared to the thickness of the walls of the receiving end 823. The walls of the upper end 828 can be between about 0.25 mm and about 2 mm or between about 0.5 mm and about 1 mm.

The cap 824 can be used to hermetically seal the vessel 808. The cap 824 can be coupled to the vessel 808 via screw threads that enable the cap 824 to be screwed into the top of the vessel 808. In some implementations, the cap can be press fit into the top of the vessel 808. The threads of the cap 824 can be coated with a coating 827. In some implementations, the coating 827 can be implemented as an o-ring or gasket. When the cap 824 is threaded onto the vessel 808, the coating 827 can create an airtight seal. The coating 827 can include Teflon®. In some implementations, the cap 824 includes plastic that enables the cap 824 to self-seal with the threads of the vessel 808. The cap 824 can couple with a cap removal tool that can be used to lower and remove the vessel 808 into and from the channel 804.

The vessel 808 can be a conical frustum, truncated cone, conical, or other conical shape. The walls of the vessel 808 slope in at angle 821. The angle 821 can be between about 1° and about 5°, between about 1° and about 4°, between about 2° and 4°, or between about 2.95° and about 3.00°. The angle 822 of the channel's receiving end 823 can have a slope substantially similar to the angle 821. The interior of the receiving end 823 can have a conical frustum, truncated cone, conical, or other conical shape that matches the shape of the vessel 808. The outer shaper of the channel 804 can be cylindrical. The sloped walls of the vessel 808 and the channel's receiving end 823 enable the vessel 808 to mate with the receiving end 823 and remain in intimate contact with the walls of the channel 804. The intimate contact increases the efficiency of heat transfer between the vessel 808 and the channel 804 because a gap substantially does not exist between the vessel wall and channel wall (e.g., thermal energy can be directly transferred between the vessel 808 and channel wall rather than through an air gap).

Vessels 808 and channels 804 with sloped walls can also have improved (e.g., relaxed) machining tolerances. For example, a cylindrical vessel would need to be machined with a very high tolerance to mate with a cylindrical channel because gaps between the wall of the vessel and the channel create thermal inefficiencies where it is more difficult for thermal energy to transfer between the channel wall and the vessel wall. For sloped vessels and channels, tolerances are relaxed because a vessel with dimensions near the minimum allowed dimensions can sit lower in the receiving end 823 (e.g., slide further into the receiving end 823). Vessels with dimensions near the maximum allowed dimensions can sit higher in the receiving end 823 of the channel. Across the range of dimension tolerances, the vessel can remain in intimate contact with the channel wall.

Many materials expand when heated. To account for this, in some implementations with cylindrical vessels and channels, the vessel can be machined to be initially narrower than the inner diameter of the channel. This can cause a gap between the vessel and channel at the start of a scan, which can inhibit the transfer of thermal energy until the vessel expands and comes into intimate contact with the channel wall. For the example illustrated in FIG. 8(*b*) with sloped vessel and channel walls, the outer diameter of the vessel can be substantially the same as the inner diameter of the channel. In this example, the vessel is in intimate contact with the channel at the beginning of the scan. As the vessel is heated and expands, the vessel diameter expands, pushing the vessel towards the top of the channel. However, because the vessel and channel walls are both sloped at the same angle, the vessel slides up along the channel wall and remains in intimate contact with the channel wall. The sloped walls of the vessel and the channel enable the vessel to remain in constant, intimate contact with the channel wall throughout the scan. Because the vessel 808 remains in contact with the channel wall throughout the scan there is a more consistent transfer of heat between the vessel 808 and channel 804 when compared to systems that employ cylindrical vessels and channels.

Therapies

Examples of cancer therapies are well known in the art and include surgery, radiation therapy, hormonal therapy, chemotherapy, immunotherapy or combinations thereof. Immunotherapeutic agents include antibodies, radioimmunoconjugates and immunocytokines. Any one or more therapeutic drugs disclosed below may be included in the methods described herein.

Classes of chemotherapeutic agents can include alkylating agents, platinum agents, taxanes, vinca agents, anti-estrogen drugs, aromatase inhibitors, ovarian suppression agents, VEGF/VEGFR inhibitors, EGF/EGFR inhibitors, PARP inhibitors, cytostatic alkaloids, cytotoxic antibiotics, antimetabolites, endocrine/hormonal agents, bisphosphonate therapy agents and targeted biological therapy agents (e.g., therapeutic peptides described in U.S. Pat. No. 6,306, 832, WO 2012007137, WO 2005000889, WO 2010096603 etc.).

Specific chemotherapeutic agents can include cyclophosphamide, fluorouracil (or 5-fluorouracil or 5-FU), methotrexate, edatrexate (10-ethyl-10-deaza-aminopterin), thiotepa, carboplatin, cisplatin, taxanes, paclitaxel, protein-bound paclitaxel, docetaxel, vinorelbine, tamoxifen, raloxifene, toremifene, fulvestrant, gemcitabine, irinotecan, ixabepilone, temozolmide, topotecan, vincristine, vinblastine, eribulin, mutamycin, capecitabine, capecitabine, anastrozole, exemestane, letrozole, leuprolide, abarelix, buserlin, goserelin, megestrol acetate, risedronate, pamidronate, ibandronate, alendronate, denosumab, zoledronate, trastuzumab, tykerb, anthracyclines, bevacizumab, or combinations thereof.

Combinational chemotherapeutic therapies can include AT: Adriamycin® (Doxorubicin) and Taxotere® (Docetaxel); AC: Adriamycin®, Cytoxan® (Cyclophosphamide); AC+Taxol®; AC+Taxotere®; CMF: Cytoxan®, Methotrexate, 5-fluorouracil; CU: Cytoxan®, Ellence® (Epirubicin), and fluorouracil; EC: Ellence®, Cytoxan®; FAC: 5-fluorouracil, Adriamycin®, and Cytoxan®; GET: Gemzar® (Gemcitabine), Ellence®, and Taxol®; TC: Taxotere®, Cytoxan®; TC: Taxotere®, Paraplatin® (Carboplatin); TAC: Taxotere®, Adriamycin®, Cytoxan® or TCH: Taxotere®, Herceptin® (Trastuzumab), and Paraplatin. Additional combination chemotherapeutic therapies for metastatic HBOC can include: Taxol and Xeloda® (Capecitabine); Taxotere and Xeloda®; Taxotere and Paraplatin®; Taxol® and Paraplatin®; Taxol® and Gemzar®; Abraxane® (Protein-bound Paclitaxel) and Xeloda®; Abraxane® and Paraplatin®; Camptosor® (Irinotecan) and Temodar® (Temozolomide); Gemzar® and Paraplatin® or Ixempra® (Ixabepilone) and Xeloda®. In some embodiments, the chemotherapeutic agents include cyclophosphamide and 5-fluorouracil or include methotrexate, cyclophosphamide and 5-fluorouracil.

The combination therapy agents described here may be administered singly or in a cocktail containing said agents or one of the agents with other therapeutic agents, including but not limited to, immunosuppressive agents, potentiators and side-effect relieving agents. The therapeutic agents can be administered intravenously or otherwise systemically by injection intramuscularly, subcutaneously, intrathecally or intraperitoneally.

As with the use of other chemotherapeutic drugs, the individual patient will be monitored in a manner deemed appropriate by the treating physician. Typically, no additional drug treatments will occur until, for example, the patient's neutrophil count is at least 1500 cells/mm$^3$. Dosages can also be reduced if severe neutropenia or severe peripheral neuropathy occurs, or if a grade 2 or higher level of mucositis is observed, using the Common Toxicity Criteria of the National Cancer Institute.

In some embodiments, the therapeutic agent comprises one or more of anti-HER-2 therapies, anti-EGFR tyrosine kinase inhibitors, PI3K/AKT/mTor pathway inhibitors, kinase inhibitors, BRAF inhibitors, ALK/MET inhibitors, ERBB2 antagonists, and RAF/MEK/ERK inhibitors. In certain embodiments, the EGFR tyrosine kinase inhibitor is gefitinib or erlotinib. In certain embodiments, the anti-EGFR therapy is cetuximab. In some embodiments of the method, the anti-HER-2 therapy is trastuzumab or lapatinib.

In some embodiments, the chemotherapeutic agent(s) comprise one or more of BRAF inhibitors, SF3b complex inhibitors, dopamine agonists, pasireotide (Signifor®), cyproheptadine (Periactin®), steroidogenesis inhibitors, Mifepristone (Korlym®), PI3K/AKT/mTOR pathway inhibitors, GnRH antagonists, and WNT signaling pathway inhibitors.

Examples of kinase inhibitors include but are not limited to crizotinib, afatinib, Axitinib, bevacizumab, Bosutinib, Cetuximab, Dasatinib, Erlotinib, Fostamatinib, Gefitinib, Imatinib, Lapatinib, Lenvatinib, Nilotinib, Panitumumab, Pazopanib, Pegaptanib, Ranibizumab, Ruxolitinib, Sorafenib, Sunitinib, Trastuzumab, and Vemurafenib.

Examples of BRAF inhibitors include, but are not limited to GDC-0879, SB590885, Encorafenib, RAF265, TAK-632, PLX4720, CEP-32496, AZ628, Sorafenib Tosylate, Sorafenib, Vemurafenib (Zelboraf) and Dabrafenib (GSK2118436).

Examples of RAF/MEK/ERK inhibitors include, but are not limited to Vemurafenib (Zelboraf) and Dabrafenib (GSK2118436), Encorafenib, TAK-632, PLX4720, MLN2480, Cobimetinib (GDC-0973), MEK 162, R05126766, GDC-0623, VTX11e, Selumetinib (AZD6244), PD0325901, Trametinib (GSK1120212), U0126-EtOH, PD184352 (CI-1040), Refametinib, PD98059, BIX02189, Binimetinib, Pimasertib (AS-703026), SL327, BIX02188, AZD8330, TAK-733, PD318088, SCH772984, and FR 180204.

Examples of PI3K/AKT/mTor pathway inhibitors include, but are not limited to BKM120, BEZ235, Pictilisib (GDC-0941), LY294002, CAL-101 (Idelalisib), GNE-317, PI-3065, HS-173, PI-103, NU7441, GSK2636771, VS-5584, CZC24832, Duvelisib, TG100-115, A66, YM201636, CAY10505, GSK1059615, PF-04691502, PIK-75, PIK-93, AS-605240, BGT226, AZD6482, Voxtalisib, Alpelisib, CUDC-907, IC-87114, Omipalisib, TG100713, Gedatolisib, CH5132799, PKI-402, BAY 80-6946, TGX-221, XL147, PIK-90, PIK-293, PIK-294, 3-Methyladenine, Quercetin, Wortmannin, ZSTK474, AS-252424, AS-604850, everolimus, and Apitolisib.

Examples of SF3b complex inhibitors include, but are not limited to spliceostatin A. Examples of dopamine agonists include, but are not limited to cabergoline and bromocriptine (Parlodel®). Examples of steroidogenesis inhibitors include, but are not limited to ketoconazole, aminoglutethimide, etomidate, metyrapone, and mitotane.

Examples of ERBB2 antagonists include, but are not limited to Lapatinib, Canertinib, CP-724,714, AZD8931, AEE788, Tyrphostin AG 879, Mubritinib, and Pertuzumab. Examples of ALK inhibitors include, but are not limited to Crizotinib, TAE684, Alectinib, Ceritinib, AP26113, AZD3463, and ASP3026.

Examples of MET inhibitors include, but are not limited to Crizotinib, PHA-665752, SU11274, SGX-523, BMS-777607, JNJ-38877605, Tivantinib, PF-04217903, MGCD-265, Capmatinib, AMG 208, MK-2461, AMG 458, NVP-BVU972, and Tepotinib.

Examples of GnRH antagonists include, but are not limited to cetrorelix, ganirelix, abarelix, degarelix, elagolix, relugolix (TAK-385), KLH-2109, and ASP-1707.

Examples of WNT signaling pathway inhibitors include, but are not limited to ICG-001, iCRT3, iCRT5, iCRT14, BC21, NC043 (15-oxospiramilactone), PKF115-584, CGP049090, PKF118-310, Thiazolidinediones (Δ2TG and STG28), Murrayafoline A, OSU03012, 3,6-dihydroxyflavone, PNU-7465431, CCT036477, CCT070535, CCT031374, and non-steroidal anti-inflammatory drugs (NSAIDs).

Examples of other therapeutic drugs useful for treating brain cancers include, but are not limited to temozolomide, procarbazine, carmustine (BCNU), lomustine (CCNU), vincristine, irinotecan, cisplatin, carboplatin, methotrexate, etoposide, bleomycin, vinblastine, actinomycin (Dactinomycin), cyclophosphamide, and ifosfamide.

Examples of agents that are useful in the treatment of viral infections include Acyclovir, Brivudin, Cidofovir, Famciclovir, Fomivirsen, Foscarnet, Ganciclovir, Penciclovir, Valacyclovir, Valganciclovir, Vidarabine, Amantadine, Rimantadine, Oseltamivir, Zanamivir, Adefovir dipivoxil, Emtricitabine, Entecavir, Lamivudine, Telbivudine, Tenofovir, Abacavir, didanosine, stavudine, zidovudine, efavirenz, etravirine, nevirapine, rilpivirine, atazanavir, darunavir, fosamprenavir, indinavir, nelfinavir, ritonavir, saquinavir, tipranavir, enfuvirtide, maraviroc, dolutegravir, elvitegravir, raltegravir, cobicistat, and lopinavir.

Examples of therapeutic agents that inhibit hepatitis C virus (HCV) include interferon alfacon-1, pegylated and/or non-pegylated interferon alfa-2b, peginterferon alfa-2a, ribavirin, telaprevir, boceprevir, sofosbuvir, simeprevir, daclatasvir, velpatasvir, ombitasvir, paritaprevir, ritonavir, dasabuvir, ledipasvir, elbasvir, danoprevir, grazoprevir, GS-7977, β-interferon, γ-interferon, amantadine, 3TC (also known as the (−) enantiomer of the nucleoside analogue cytosine-1,3-oxathiolane), and inhibitors that target the HCV life cycle, including but not limited to, helicase, polymerase, metalloprotease or internal ribosome entry site (IRES).

Examples of inhibitors that target the HCV life cycle include heterocyclic-substituted carboxamides (described in U.S. Pat. No. 5,633,388) that interfere with the helicase activity of the NS3 protein; the phenanthrenequinone reported in Chu et al., *Tet. Lett.* 7229-7232 (1996), which inhibits HCV NS3 protease in vitro; morpholinylcarbonyl-benzoyl-peptide analogues (WO 1995/33764); NS5A/5B substrate-based peptide analogues (WO 1998/17679); thiazolidine derivatives (Brown-Driver et al., *Antiviral Research* 30(1), A23 (1996)) which inhibit HCV protease; and other peptide inhibitors of HCV NS3 protease (Steinkühler et al., *Biochemistry* 37:8899-8905 (1998); Ingallinella et al., *Biochemistry* 37:8906-8914 (1998)).

Classes of antibiotics that are useful in the treatment of bacterial infections include Penicillins such as penicillin and amoxicillin, Cephalosporins such as cephalexin (Keflex), Macrolides such as erythromycin (E-Mycin), clarithromycin (Biaxin), and azithromycin (Zithromax), Fluoroquinolones such as ciprofolxacin (Cipro), levofloxacin (Levaquin), and ofloxacin (Floxin), Sulfonamides such as co-trimoxazole (Bactrim) and trimethoprim (Proloprim), Tetracyclines such as tetracycline (Sumycin, Panmycin) and doxycycline (Vibramycin), Aminoglycosides such as gentamicin (Garamycin) and tobramycin (Tobrex), and Colistin.

Examples of agents that are useful in the treatment of fungal infections include Caspofungin, rifabutin, Fluconazole, zidovudine, acetaminophen, loratadine, warfarin, tacrolimus, Anidulafungin, Posaconazole, ketoconazole, meperidine, didanosine, Voriconazole, Rifampin, cisapride, cyclosporine, Itraconazole, diphenhydramine, phenytoin, carbamazepine, flucytosine, digoxin, and Micafungin.

In therapeutic applications, the dosages of the agents used in accordance with the present technology vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, and also preferably causing complete regression of the disease or condition. An effective amount of a therapeutic agent is that which provides an objectively identifiable improvement as noted by the clinician or other qualified observer. Regression of a tumor in a patient is typically measured with reference to the diameter of a tumor. Decrease in the diameter of a tumor indicates regression. Regression is also indicated by failure of tumors to reoccur.

Methods of the Present Technology

The following discussion is presented by way of example only, and is not intended to be limiting.

In one aspect, the present technology provides methods for detecting thermostable variants of proteins and/or metabolites in a biological sample (e.g., tissue, whole blood, plasma or serum) comprising: (a) loading an undiluted fraction of the biological sample into the differential scanning calorimeter of the present technology; (b) generating a signature DSC thermogram from the undiluted fraction of the biological sample; and (c) detecting thermostable variants of proteins and/or metabolites when at least one alteration is present in the signature DSC thermogram of the biological sample relative to that observed in a DSC thermogram generated from a normal control sample. The sample may be obtained from a patient that is suspected of having, or is at risk for a disease or condition. In some embodiments, the disease or condition is selected from the group consisting of: cancer (e.g., breast cancer, brain cancer, myeloma, acute myeloblastic promyelocyte leukemia, Waldenstrom's disease, etc.), a pathogenic infection, diabetes mellitus, cardiovascular disease, neurodegenerative disease (e.g., Alzheimer's disease, Amyotrophic lateral sclerosis, Friedreich's ataxia, Huntington's disease, Lewy body disease, Parkinson's disease, spinal muscular atrophy etc.), and rheumatic disease. In certain embodiments, the patient is suffering from stage 0, stage I, stage II, stage III, or stage IV cancer. Additionally or alternatively, in certain embodiments, the patient lacks any detectable rigid tumor mass (e.g., in soft breast tissue, brain tissue, etc.).

In some embodiments, the rheumatic disease is selected from the group consisting of: osteoarthritis, rheumatoid arthritis, ankylosing spondylitis, Sjögren's syndrome, Antinuclear Antibodies (ANA), Antiphospholipid Syndrome, Calcium Pyrophosphate Deposition (CPPD), Carpal Tunnel Syndrome, Cryopyrin-Associated Autoinflammatory Syndrome (CAPS), Dermatomyositis, familial Mediterranean fever, fibromyalgia, giant cell arteritis, glucocorticoid-induced osteoporosis, gout, granulomatosis with Polyangitis (Wegener's), hypermobility, Hyperimmunoglobulin D Syndrome, inflammatory myopathies, juvenile arthritis, scleroderma, Lyme disease, metabolic myopathies, osteonecrosis, osteonecrosis of the jaw (ONJ), osteoporosis, Paget's disease, PFAPA (Periodic Fever, Aphthous Stomatitis, Pharyngitis, Adenitis Syndrome), polymyalgia rheumatic, psoriatic arthritis, Raynaud's phenomenon, reactive arthritis, spinal stenosis, spondyloarthritis, Systemic Lupus Erythematosus, Takayasu's arteritis, Tendinitis & bursitis, Tumor Necrosis Factor Receptor Associated Periodic Syndrome, and vasculitis.

The pathogenic infection may be bacterial, viral or fungal. In some embodiments, the pathogenic infection is caused by *Clostridium difficile*, carbapenem-resistant Enterobacteriaceae, multidrug resistant *Acinetobacter*, multidrug resistant *Campylobacter*, flucoazole resistant *Candida*, extended spectrum beta-lactamase-producing Enterobacteriaceae, Vancomycin Resistant Enterococci, Multi-drug resistant *Pseudomonas aeruginosa*, drug resistant Non-typhoidal *Salmonella*, drug resistant *Salmonella* serotype *Typhi*, drug resistant *Shigella*, Methicillin-Resistant *Staphylococcus aureus*, drug resistant *Streptococcus pneumoniae*, or drug resistant *Mycobacterium tuberculosis*. In other embodiments, the pathogenic infection is caused by hepatitis B virus, hepatitis C virus, HIV, Human Papilloma Virus, or Epstein Barr virus.

Additionally or alternatively, in some embodiments, the biological sample is plasma, serum, whole blood, or tissue (i.e., non-homogenized, unprocessed tissue). In certain embodiments, the volume of the biological sample is no more than 20 µL. In other embodiments, the volume of the biological sample is about 20-50 or about 50-125 µL.

In any of the above embodiments of the methods of the present technology, the at least one alteration present in the signature DSC thermogram of the biological sample may comprise one or more of: an increase in $\Delta T_m$ at half max (integral melting width) by at least 10%, a reduction in excess heat capacity (dQ/dT) by about 10-20%, a 5-8° C. increase in main peak $T_m$, or detection of a new shoulder or peak at 58-60° C. In certain embodiments, the concentration of proteins that melt at 56-63° C. with a maximum $T_m$ of 59±1° C. is 650±120 µg/ml, 120±50 µg/ml, or 150±60 µg/ml.

Additionally or alternatively, in some embodiments of the methods disclosed herein, the at least one alteration present in the signature DSC thermogram of the biological sample may comprise one or more of: detection of new shoulders or peaks at 69° C. and 75° C., an increase in the integral melting width of the dual peak by at least 200%, and a reduction in excess heat capacity (dQ/dT) by about 50%.

Additionally or alternatively, in some embodiments of the methods disclosed herein, the at least one alteration present in the signature DSC thermogram of the biological sample may comprise one or more of: detection of a new peak at 70° C., 75° C., and/or 80.7-83.3° C.; detection of a sharp peak at 70±1.0° C.; an increase in Y-Globulin concentration by at least 400%; an increase in $\Delta C$ excess (dQ/dT) of Y-Globulin by about 400%; an increase in main peak width by at least 250%; and a 20-35% decrease in $\Delta C$ excess of albumin.

Additionally or alternatively, in some embodiments of the methods disclosed herein, the at least one alteration present in the signature DSC thermogram of the biological sample may comprise one or more of: detection of a new peak at 57±1.3° C., an increase in Bence Jones protein concentration by at least 200%, and a reduction of albumin concentration by about 15-20%.

Additionally or alternatively, in some embodiments of the methods disclosed herein, the at least one alteration present in the signature DSC thermogram of the biological sample may comprise detection of a new peak or shoulder at 62° C., 66° C. and/or 85° C.

Additionally or alternatively, in some embodiments of the methods disclosed herein, the at least one alteration present in the signature DSC thermogram of the biological sample may comprise detection of a power peak at 66° C.

Additionally or alternatively, in some embodiments of the methods disclosed herein, the at least one alteration present in the signature DSC thermogram of the biological sample may comprise detection of a new peak or shoulder at 55° C., 67° C., and/or 85.5° C.

In another aspect, the present disclosure provides a method for identifying a subject as having, or at risk for cancer comprising (a) loading an undiluted fraction of a biological sample obtained from the subject into the differential scanning calorimeter disclosed herein; (b) generating a signature DSC thermogram from the undiluted fraction of the biological sample; and (c) identifying the subject as having, or at risk for cancer when at least one alteration is present in the signature DSC thermogram of the biological sample relative to that observed in a DSC thermogram generated from a normal control sample. The biological sample may be plasma, serum, whole blood, or tissue (i.e., non-homogenized, unprocessed tissue). In some embodiments, the cancer is breast cancer, brain cancer, acute myeloblastic promyelocyte leukemia, Waldenstrom's disease, multiple myeloma G, multiple myeloma A, or Bence Jones myeloma.

In some embodiments of the method, the at least one alteration present in the signature DSC thermogram of the biological sample may comprise one or more of: an increase in $\Delta T_m$ at half max (integral melting width) by at least 10%, a reduction in excess heat capacity (dQ/dT) by about 10-20%, a 3-8° C. increase in main peak $T_m$, or detection of a new shoulder or peak at 58-60° C. In a further embodiment, the concentration of proteins that melt at 56-63° C. with a maximum $T_m$ of 59±1° C. is 650±120 µg/ml, 120±50 µg/ml, or 150±60 µg/ml.

In certain embodiments of the method, the at least one alteration present in the signature DSC thermogram of the biological sample may comprise one or more of: detection of new shoulders or peaks at 69° C. and 75° C., an increase in the integral melting width of the dual peak by at least 200%, and a reduction in excess heat capacity (dQ/dT) by about 50%.

In other embodiments of the method, the at least one alteration present in the signature DSC thermogram of the biological sample may comprise one or more of: detection of a new peak at 70° C., 75° C., and/or 80.7-83.3° C.; detection of a sharp peak at 70±1.0° C.; an increase in Y-Globulin concentration by at least 400%; an increase in ΔC excess (dQ/dT) of Y-Globulin by about 400%; an increase in main peak width by at least 250%; and a 20-35% decrease in ΔC excess of albumin.

In some embodiments of the method, the at least one alteration present in the signature DSC thermogram of the biological sample may comprise one or more of: detection of a new peak at 57±1.3° C., an increase in Bence Jones protein concentration by at least 200%, and a reduction of albumin concentration by about 15-20%.

In some embodiments of the method, the at least one alteration present in the signature DSC thermogram of the biological sample may comprise detection of a new peak or shoulder at 62° C., 66° C. and/or 85° C.

In certain embodiments of the method, the at least one alteration present in the signature DSC thermogram of the biological sample may comprise detection of a power peak at 66° C.

Additionally or alternatively, in some embodiments of the method, the subject does not exhibit any detectable rigid tumor mass.

Additionally or alternatively, in some embodiments, the method further comprises administering to the subject an effective amount of radiation therapy, hormonal therapy, chemotherapy, immunotherapy, surgery, or combinations thereof. The use of any one or more anti-cancer therapeutic drugs disclosed herein are encompassed by the methods of the present technology.

In another aspect, the present disclosure provides a method for diagnosing a subject as having a pathogenic infection comprising (a) loading an undiluted fraction of a biological sample obtained from the subject into the differential scanning calorimeter disclosed herein; (b) generating a signature DSC thermogram from the undiluted fraction of the biological sample; and (c) diagnosing the subject with a pathogenic infection when at least one alteration is present in the signature DSC thermogram of the biological sample relative to that observed in a DSC thermogram generated from a normal control sample. The pathogenic infection may be bacterial, fungal, or viral. In some embodiments, the pathogenic infection is caused by *Clostridium difficile*, carbapenem-resistant Enterobacteriaceae, multidrug resistant *Acinetobacter*, multidrug resistant *Campylobacter*, flucoazole resistant *Candida*, extended spectrum beta-lactamase-producing Enterobacteriaceae, Vancomycin Resistant Enterococci, Multi-drug resistant *Pseudomonas aeruginosa*, drug resistant Non-typhoidal *Salmonella*, drug resistant *Salmonella* serotype *Typhi*, drug resistant *Shigella*, Methicillin-Resistant *Staphylococcus aureus*, drug resistant *Streptococcus pneumoniae*, or drug resistant *Mycobacterium tuberculosis*. In other embodiments, the pathogenic infection is caused by hepatitis B virus, hepatitis C virus, HIV, Human Papilloma Virus, or Epstein Barr virus.

In some embodiments, the at least one alteration present in the signature DSC thermogram of the biological sample comprises one or more of: detection of a double peak at 67° C. and 70° C., an increase in ΔT$_m$ at half max (integral melting width) by at least 100%, a reduction in excess heat capacity (dQ/dT) by 12-45% and 22-60% for peaks 67° C. and 70° C. compared to dQ/dT of Albumin; and detection of a new weak shoulder at 84° C.

In some embodiments, the at least one alteration present in the signature DSC thermogram of the biological sample comprises detection of a new peak or shoulder at 55° C., 67° C., and/or 85.5° C.

In some embodiments, the method further comprises administering to the subject an effective amount of an antibacterial agent, an antiviral agent, an antifungal agent, or any combination thereof. The use of any antibacterial agent, antiviral agent, or antifungal agent disclosed herein are encompassed by the methods of the present technology. By way of example, but not by way of limitation, in some embodiments, the method further comprises administering to the subject an effective amount of one or more of interferon alfacon-1, pegylated and/or non-pegylated interferon alfa-2b, peginterferon alfa-2a, ribavirin, telaprevir, boceprevir, sofosbuvir, simeprevir, daclatasvir, velpatasvir, ombitasvir, paritaprevir, ritonavir, dasabuvir, ledipasvir, elbasvir, danoprevir, grazoprevir, GS-7977, β-interferon, γ-interferon, amantadine, or 3TC.

In any of the above embodiments of the methods, the biological sample is plasma, serum, whole blood, or tissue. In some embodiments, the volume of the biological sample is about 50-125 μL, about 20-50 μL, or no more than 20 μL.

In one aspect, the present disclosure provides a method for detecting the onset of relapse in a patient diagnosed as having a disease or condition comprising: (a) loading an undiluted fraction of a biological sample obtained from the patient into the differential scanning calorimeter disclosed herein; (b) generating a signature DSC thermogram from the undiluted fraction of the biological sample; and (c) detecting the onset of relapse in the patient when at least one alteration is present in the signature DSC thermogram of the biological sample relative to that observed in a DSC thermogram generated from a normal control sample, wherein the at least one alteration is similar or identical to that observed in a DSC thermogram generated from a positive control sample having the disease or condition. The disease or condition may be breast cancer, brain cancer, acute myeloblastic promyelocyte leukemia, Waldenstrom's disease, myeloma, a pathogenic infection, or any other disease or condition described herein. Additionally or alternatively, in some embodiments, the method further comprises monitoring the progression of the disease or condition using the differential scanning calorimeter of the present technology.

DSC melt curve profiles provide conveniently measurable benchmarks by which to gauge the effectiveness of a therapeutic regimen. Thus, in another aspect, the present disclosure provides a method for evaluating the efficacy of a therapeutic regimen in a patient in need thereof comprising (a) loading an undiluted fraction of a biological sample obtained from the patient following administration of the therapeutic regimen into the differential scanning calorimeter disclosed herein; (b) generating a signature DSC thermogram from the undiluted fraction of the biological sample; and (c) determining the therapeutic regimen is efficacious when the signature DSC thermogram of the biological sample resembles a DSC thermogram generated from a normal control sample. In some embodiments, the patient is diagnosed with, or is at risk for a disease or condition selected from among breast cancer, brain cancer, myeloma, acute myeloblastic promyelocyte leukemia, Waldenstrom's disease, a pathogenic infection, or any disease or condition described herein. Additionally or alternatively, in some embodiments, the signature DSC thermogram of the biological sample shows at least one alteration relative to that observed in a DSC thermogram generated from a sample obtained from the patient prior to administration of the therapeutic regimen. Additionally or alternatively, in some embodiments, the method further comprises monitoring the efficacy of the therapeutic regimen using the differential scanning calorimeter of the present technology. The therapeutic regimen may be maintained, discontinued, or subsequently modified based on the DSC melt curve profiles observed in the patient during or after the administration of the therapeutic regimen.

In another aspect, the methods described herein are useful in identifying patient populations that exhibit different degrees of sensitivities to a therapeutic agent (e.g., a therapeutic agent disclosed herein or known in the art). Age, gender, height, weight, ethnicity, family history of genetic disorders, immunocompromised status, and medical history are non-limiting examples of factors that can impact responsiveness of a patient to a particular therapeutic agent.

Alterations in DSC melt curve profiles (i.e., DSC thermograms) can be used to classify patients based on their responsiveness to a specific dose of a therapeutic agent. In some embodiments, a patient may be responsive, non-responsive, or hyper-responsive to a therapeutic agent at a specific dose or a range of doses. Determining patient sensitivity to a therapeutic agent is useful in optimizing therapeutic efficacy and reducing side effects associated with the therapeutic agent. In certain embodiments, the dose of the therapeutic agent may be adjusted to achieve therapeutic efficacy and/or minimize side effects based on alterations in DSC melt curve profiles (generated using the differential scanning calorimeter of the present technology) in treated patients. In other embodiments, a therapeutic agent may be supplemented with an additional therapeutic agent to achieve therapeutic efficacy and/or minimize side effects based on alterations in DSC melt curve profiles (generated using the differential scanning calorimeter of the present technology) in treated patients. In another embodiment, treatment with a therapeutic agent may be temporarily or completely discontinued to achieve therapeutic efficacy and/or minimize side effects based on alterations in DSC melt curve profiles (generated using the differential scanning calorimeter of the present technology) in treated patients.

Efficacy of treatment of disease can be assessed, for example by measuring disease progression, disease remission, symptom severity, reduction in pain, quality of life, dose of a medication required to sustain a treatment effect, level of a disease marker or any other measurable parameter appropriate for a given disease being treated. It is well within the ability of one skilled in the art to monitor efficacy of treatment by measuring any one of such parameters, or any combination of parameters using the devices and methods disclosed herein.

EXAMPLES

The present technology is further illustrated by the following examples, which should not be construed as limiting in any way. For example, the devices and methods of the present technology may be applied to any disease or condition, including but not limited to, breast cancer, brain cancer, myeloma, acute myeloblastic promyelocyte leukemia, Waldenstrom's disease, pathogenic infections, or any disease or condition described herein.

Example 1: General Methods and Procedures

Blood was collected at the Mammalogy Centre, Institute of Clinical Oncology, in Tbilisi, Georgia, during post-surgery from breast cancer patients diagnosed according to histology, disease stage, nodal involvement, and tumor size.

Plasma was isolated using whole blood centrifugation for 10 minutes at 2000×g at 4° C., in the presence of K2-EDTA. The undiluted supernatant was used for calorimetric studies. Breast cancer plasma or serum samples (n=42) and healthy control plasma/serum samples (n=154) were analyzed using a differential scanning microcalorimeter (DSC) having a sensitivity of 0.1 µW. DSC measurements were taken immediately after blood collection and centrifugation. The operational measuring vessel volume was 125 µl; the dry sample biomass in a vessel was within the range 9.5 to 10.0 mg, the employed scanning rate was 1.0° per minute, and the measured temperature range was from 25° C. to 98° C. The accuracy of the temperature measurements was <0.05° C. The maximum measuring error in determining melting enthalpy ($\Delta H_m$) and heat increment dQ/dT ($DC^{max}$) was <12%. The microcalorimeter (DSC) processor was equipped with relevant software needed for determining the melting thermodynamic parameters of blood plasma/serum, and the calorimetric curves were plotted and deconvoluted with Origin 9.0 software (OriginLab, Northampton, MA). The weight content of total biomass in both normal and cancer samples was determined by biochemical methods or via the DSC device disclosed herein. Dry biomass (plasma/serum) weight in the measuring vessels was determined at 105° C., and the ash mass of plasma/serum was determined at 450-500° C. in quartz containers.

The assayed patient population comprised 3 post-surgery groups of female patients with breast carcinoma (BC) without any distant metastases (i.e., 3 women after ablation of a single breast (49, 52, and 56 year old women from group I, from one month to 14 or 15 years post-surgery), 3 women after lumpectomy (53, 54, and 58 year old women from group II, from one month to 17 years post-surgery), 8 patients with BC stages I-IV (30-75 year old women from group III, 5 years post-surgery), 3 healthy adult women who were daughters of the 49, 54 and 56 year old patients (group 4), and 154 healthy volunteers (20-75 year old women, group 5). The observed curve profiles were similar within each group, and the only notable difference was in peak intensities. The endotherm maxima coincided with 1° C. accuracy for a given disease stage. All patients were monitored since 1998-2000. Data for the 49 and 56 year old BC women from group I with a tumor size of 22 and 20 mm, respectively, and the 54 year old BC woman from group II with a tumor size of 10 mm were evaluated.

DSC was performed on plasma/serum samples obtained from 8 other patients without metastasis in other organs after lumpectomy during the last 5 years. These DSC curves were similar to the data represented by the dash line in FIG. 1. The DSC curves of plasma samples obtained from 28 patients before surgery (size of tumor tissue ranging from 8 to 48 mm) fully correlated with the clinical diagnosis for each patient. Deconvolution of plasma/serum for healthy controls was made on the basis of two requirements: (a) melting of major plasma proteins take place independently from each other (Khachidze D G, Monaselidze J R. *Biofizika* 45: 325-328 (2000)); and (b) clinical data regarding albumin concentration for a particular subject and albumin melting enthalpy (Privalov P L. *Adv Protein Chem* 35: 1-104 (1982)) were taken into account in deconvolution analyses.

Example 2: Use of the DSC Device and Methods of the Present Technology to Detect Breast Cancer and/or Identify Subjects at Risk for Breast Cancer This Example demonstrates that the DSC device and methods of the present technology are useful in detecting breast cancer in subjects, and/or identifying subjects that are at-risk for developing breast cancer.

Among women, breast cancer is the most commonly diagnosed cancer after non-melanoma skin cancer and is the second leading cause of cancer-related death after lung cancer. Tumors are frequently detected as a rigid mass area within a pliant tissue. Indeed, mammographic density of breast tissue (MD) is a major risk factor for the development of breast carcinoma (Provenzano et al., *BMC Med.* 2008; 6:11). Most but not all prior studies (Sala et al., *Eur Radiol.* 2000; 10(1):157-61) have reported a strong association of MD with large tumors versus small tumors (Boyd et al., *N Engl J Med.* 2007; 356(3):227-36). However, patients with fibrotic stiff lesions have a poor prognosis (Colpaert et al., *Am J Surg Pathol.* 2001; 25:1557-8). Breast cancer is a very heterogeneous disease at both histological and molecular levels. At least six distinct subtypes have been described on the basis of gene expression profiling (Hennighausen L, Robinson G W. *Nat Rev Mot Cell Biol.* 2005; 6(9):715-25). Conventional cancer screening methods, such as X-ray imaging, pose undesirable health risks to female patients, particularly young and pregnant women, or breast cancer patients who are recovering from surgery. Analysis of estrogen, progesterone, epidermal growth factor, and other biomarkers (e.g., TNW and TNC) require samples derived from cancer tissues via invasive biopsy procedures.

Figure 2:
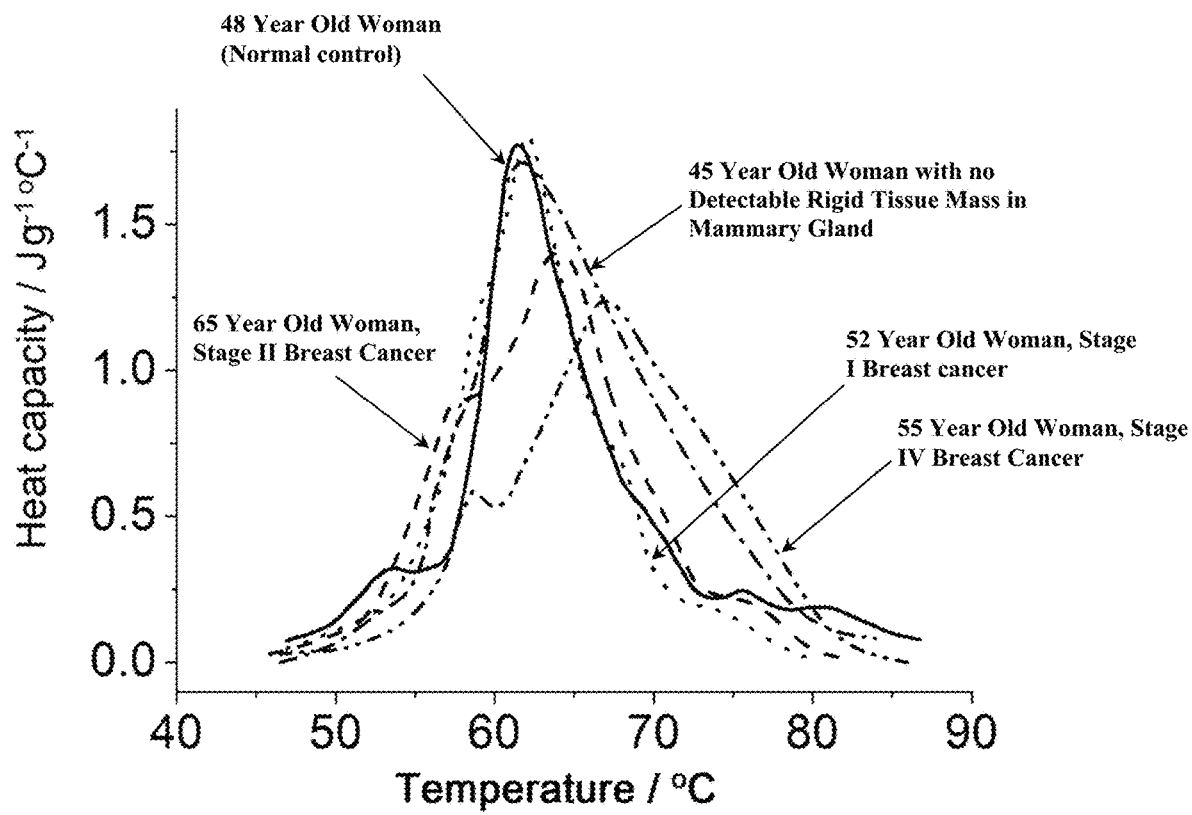
FIG. 2 shows heat absorption curves (heat capacity dQ/dT, J $g^{-1°}$ $C.^{-1}$) as a function of temperature of blood plasma samples obtained from female patients, recalculated per gram biomass: Solid line: 48 year old woman (normal control), Mass (hereinafter, M) (protein)=9.2 mg; Dash dot line: 45 year old woman that is stage 0 carcinoma in situ-positive via histopathological assay and has no detectable rigid tissue mass in the mammary glands via X-ray, MRI, or CAT scan, M (protein)=8.8 mg; Dot line: 52 year old woman with stage I breast cancer, M (protein)=9.6 mg; Dash line: 65 year old woman with stage II breast cancer, M (protein)=9.4 mg; Dash dot dot line: 55 year old woman with stage IV breast cancer, M (protein)=10.0 mg

FIG. 2 shows the blood plasma DSC curves of a healthy female patient (control) and breast cancer patients at different stages. FIG. 2 demonstrates that the melting curve profiles of the control and breast cancer patients differed significantly from each other. Differences were also observed between the curves of the breast cancer patients at different stages. Significant changes were observed in the intensities of the heat absorption peaks, their lateral shift along the temperature scale towards higher temperatures, and sharp increases in $\Delta T_m$.

In particular, the intensity ($DC^{max}$) of the main peak at 62±1° C. (corresponding to albumin fatless fraction) decreased in stage I, II, and IV breast cancer patients relative to that observed in the healthy control patient. The $T_m$ of the albumin fatless fraction increased in stage I, II, and IV breast cancer patients by about 2° C., 4° C. and 6° C., respectively. The shoulder intensity at 70° C. (corresponding to the melting of c-globulins) also varied between the breast cancer patients and the healthy control patient. Further, significant increases of about 40%-100% in the integral melting width (i.e., the (delta) $T_m$ at half max) were observed in the plasma samples of breast cancer patients. A weak shoulder appeared at the low-temperature side of the albumin peak at 56-59° C. in a stage 0 patient (carcinoma in situ-positive) that lacked detectable rigid tumor mass in the breast tissue. This shoulder converted into a clear peak at 58±1° C. in stage III and stage IV breast cancer patients with detectable metastases in the lymph nodes. In contrast, a shoulder or peak in the temperature range 55-60° C. was completely absent in the healthy control patient. Deconvolution of the DSC curve of the healthy control patient showed six independent transitions (FIG. 6(d)). The first transition corresponds to the melting of the D domains of fibrinogen; the second transition to the melting of fatless/non-ligand fractions of albumin; the third transition to haptoglobin, Fab fragment of immunoglobulin G, α1-antitrypsin, ceruloplasmin, and transferrin, which melt at around 61, 63, 64, 65 and 67° C., respectively; the fourth transition to the melting of c-globulins at 70° C.; the fifth transition to the melting of protein inhibitors; and the sixth transition to the melting of fat/ligand fraction of albumin, which includes melting of its stable fraction at $T_m$=82° C. The Gaussian deconvolution of stage IV breast cancer (FIG. 6(b)) revealed seven independent transitions (near 57, 59, 64, 68, 72, 77 and 90° C.).

Figure 6A:
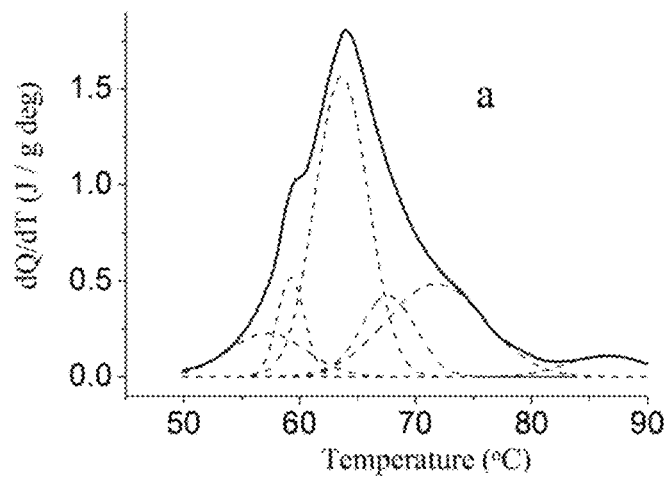
FIGS. 6(a)-(e) show deconvolution of blood plasma curves for patients with breast cancer, or at risk for breast cancer, and normal control patients.
Figure 6B:
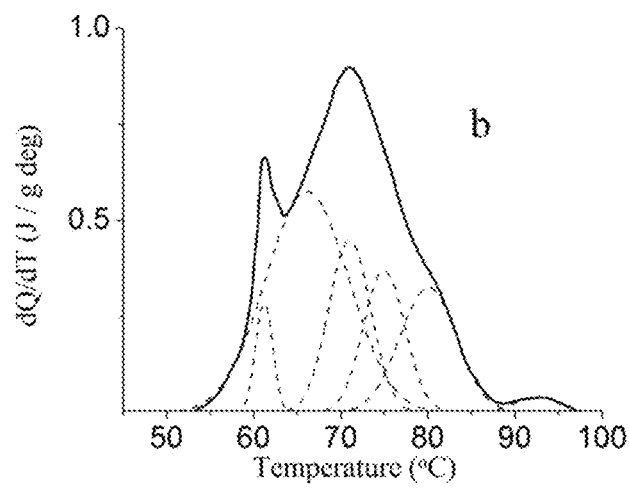
Figure 6C:
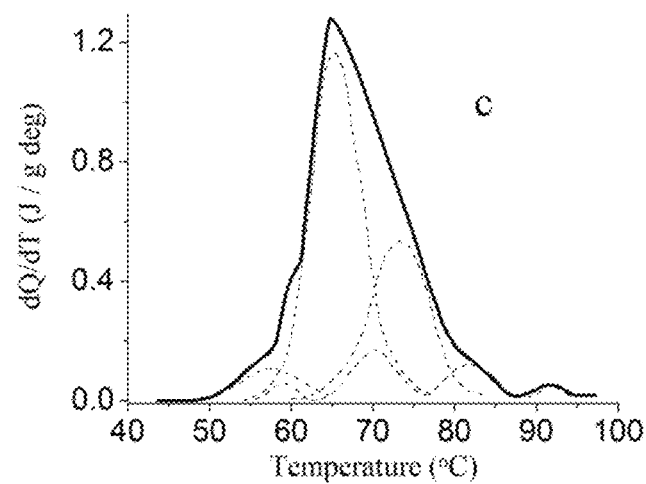
Figure 6D:
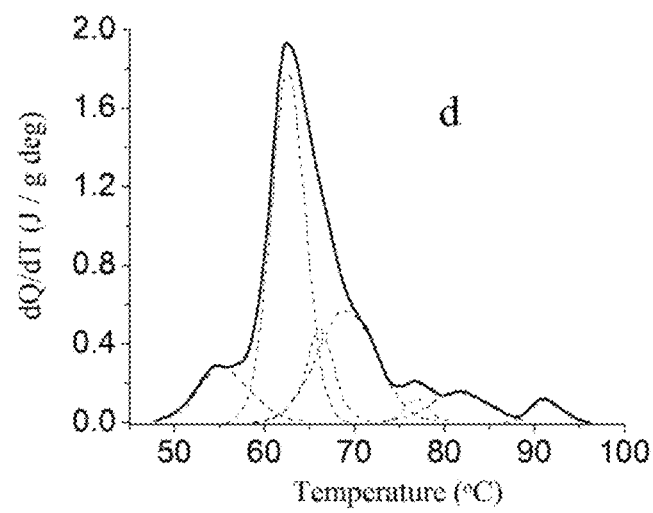
Figure 6E:
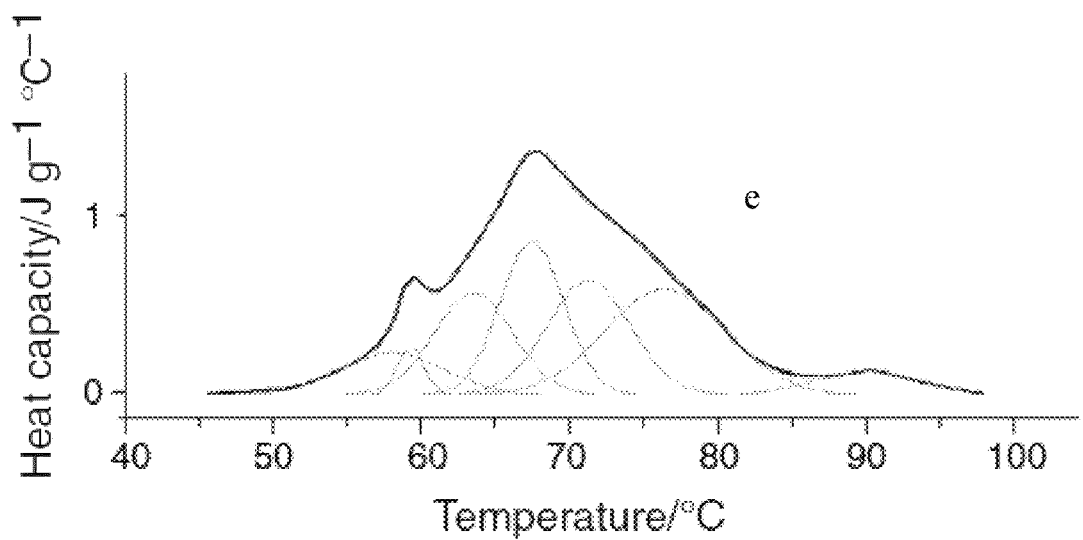

The comparison of the deconvoluted melting curves of stage III breast cancer plasma (FIG. 6(e)) with those of healthy control plasma (FIG. 6(d)) revealed an additional melting transition with parameters $T_m$=59±1° C. and $\Delta T$=2.0±0.5° C., which was not present in the deconvoluted melting curves of the healthy control. Deconvolution of the DSC curve of a plasma/serum sample always yielded a weak clear peak in the temperature range 58-60° C., when a risk factor for breast cancer is present (FIG. 6(c)). While not wishing to be bound by theory, the shoulder or peak at 58-60° C. may represent the melting of fibronectin and tenascins. It has been previously shown that the concentrations of both fibronectin and tenascins significantly increase during cancer development (Jennifer J. et al., *Cancer* 51(6): 1142-7 (1983); Guttery D S et al., *Breast Cancer Res.* 12:R57 (2010); Brellier F et al., *BMC Clin Pathol.* 12:14 (2012). However, the narrow melting interval ($\Delta T$=2.0±0.5° C.) of the additional melting transition in the undiluted breast cancer plasma sample was unexpected, given that fibronectin in diluted samples has been shown to melt at 60 C.° with $\Delta T$=8-10° C. This observed difference may be attributed in part to the high concentration of total proteins and the higher degree of intermolecular interactions in the undiluted plasma sample.

The heat absorption deconvolution peak with $T_m$=59±1° C., $\Delta T$=2.5±0.7° C. was observed in stage II and IV breast cancer patients (FIGS. 6(a), 6(b) and 6(e)), but not in healthy control subjects (n>154 healthy female subjects, from ages 12 to 71; e.g., FIG. 6(d)). Additionally, there were significant alterations in $T_m$, $\Delta T_m$, $\Delta H_m$ and $DC^{max}$ of the main peak as well as altered heat distribution between the deconvolution peaks of breast cancer patients (FIGS. 6(a) and 6(b)) relative to that observed in healthy control subjects (FIG. 6(d)). While not wishing to be bound by theory, these shifts in thermostability profiles may be attributed to differential interactions between plasma proteins and domains within individual macromolecules. For example, it is known that human serum albumin consists of three domains, each having an independent in vitro melting temperature at 64° C., 68° C. and 78° C. (temperature range=14° C.). In blood plasma, the three domains of human serum albumin combine and create 2 independent domains, which melt cooperatively at narrow temperature ranges with $\Delta T$=5° and $\Delta T$=8°, respectively, which is indicative of a strong interaction between the domains. It is also known that the N-terminal and central fragments of albumin are in a fatless fraction in healthy human plasma. Hence, the multiple binding sites of albumin may bind metal ions, fatty acids, hormones, drugs, and in some instances, breast cancer-specific biological oncomarkers. Thus, the altered thermostability of plasma/serum proteins observed in breast cancer patients may reflect the binding of breast cancer-specific biological oncomarkers (e.g., tenascin-C (TNC) and tenascin-W (TNW)) to the fatless albumin fraction, thus weakening the interactions between the N-terminal and central albumin domains. Similarly, an increase in albumin $T_m$ by 4° C., $\Delta T_m$ by ~300%, decrease in dQ/dT by ~300% and slight changes in gamma-globulins may reflect alterations in thermostability of immunoglobulins in breast cancer plasma samples compared to healthy control subjects (FIGS. 6(a)-6(b) vs. FIG. 6(d)).

Figure 3:
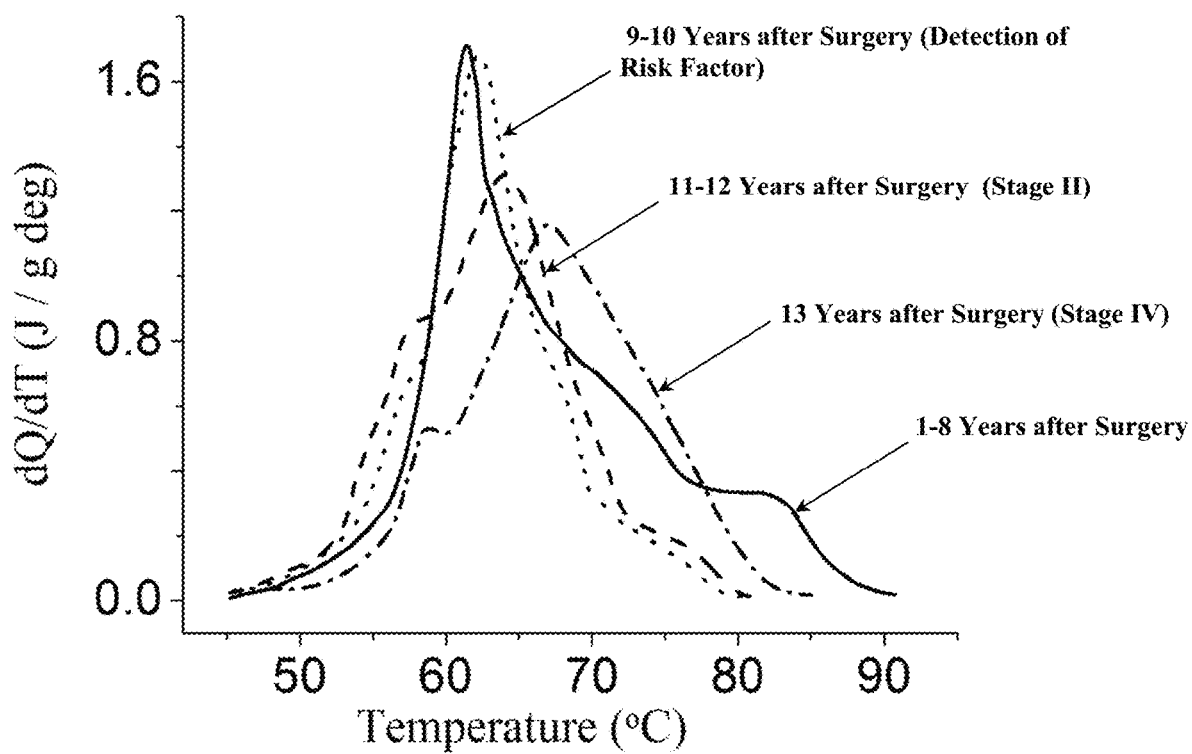
FIG. 3 shows heat absorption curves (heat capacity dQ/dT, J $g^{-1°}$ $C.^{-1}$) as a function of temperature of serum samples obtained from the same 56 year old, stage I breast cancer female patient described in FIG. 1 after surgery, recalculated per gram biomass: Solid line: 1-8 years after surgery; Dot line: 9-10 years after surgery, early evidence of risk of relapse; Dash line: 11-12 years after surgery, clinical diagnosis revealed patient was lymph node positive, and distant metastasis in lungs (stage II); Dot-dash line: 13 years after surgery, clinical diagnosis revealed patient was lymph node positive, and distant metastasis in lungs and liver (stage IV). In all the foregoing cases of control and breast cancer serum samples, the melting enthalpy was equal to 20.5±2.5 J/g dry biomass and only redistribution of heat between the endotherms was observed.

Taking into account the fact that the melting enthalpy ($\Delta H_m$) of globular proteins, including multi-domain proteins is approximately—6.0 cal/g in the temperature range of 65-70° C. (Privalov P L. *Adv Protein Chem* 35: 1-104 (1982)), the concentration of proteins that melt in the temperature interval 56-63° C. with the maximum at $T_m=59\pm1°$ C. was calculated using heath value from the area under the peak. Protein concentration is 650±120 µg/ml in stage II-IV breast cancer (FIG. 6(*b*)), 120±50 µg/ml in the case of breast cancer risk (FIGS. 6(*c*)), and 150±60 µg/ml in the case of breast cancer relapse (FIG. 3, dot line).

FIG. 1 shows the DSC curves of a healthy woman at age 30 and at age 42, and her 56 year old mother who was diagnosed with stage I ductal carcinoma. No rigid tissue mass was detected in the mammary glands of the daughter at either age. In all the above cases, the melting enthalpy was equal to 20.5±2.5 J/g dry biomass.

In the curve profile of the healthy daughter at age 30, the peak intensity (dQ/dT) at 1.52 J/g.deg and maximum at around 62±0.1° C. and $\Delta T=7.2\pm0.2°$ C. was mainly associated with the albumin fatless fraction. The shoulder in the temperature range 50-56° C. corresponded to the melting of LT1 (D) fibrinogen fragment, HT2 (D) fibrinogen fragment, and a more thermolabile part of the main albumin fraction. The weak peak at 91.5±0.2° C. corresponded to the melting of HT2 (E) fibrinogen fragment (dash line). The dot line corresponds to the DSC curve of the 56 year old mother diagnosed with stage I ductal carcinoma (with metastases in the lymph nodes) prior to surgery. A shoulder at around 59-61° C. was observed in the thermogram of the 56 year old mother. Additionally, a $T_m$ increase of about 3.8-4.1° C. for the albumin main peak, and around 60% increase in the integral melting width were also observed in the thermogram of the 56 year old mother.

As shown in FIG. 1, the second curve profile of the healthy daughter at age 42 (solid line) resembled the profile of the first curve (dash line). However, a weakly expressed shoulder at 56-59° C. (i.e., less prominent than that observed in the 56 year old mother with stage I breast cancer) was observed in the thermogram of the 42 year old daughter, which represents a risk factor for developing breast cancer. Thus, the methods disclosed herein permit early identification of a patient at risk for breast cancer, even in the absence of detectable rigid tumor mass in the breast tissue of the patient.

Figure 7:
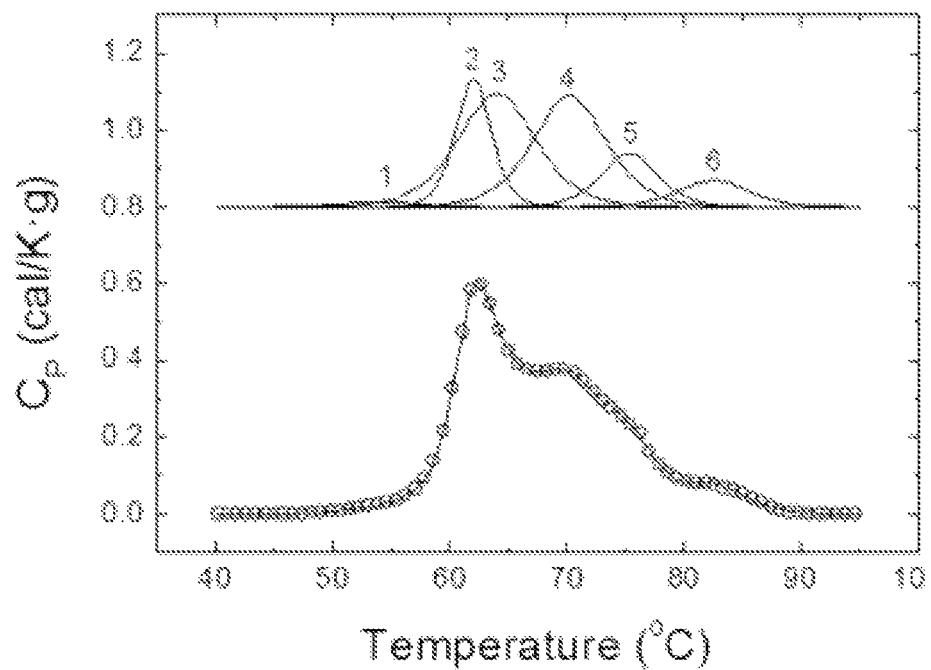
FIG. 7 shows deconvolution of a diluted serum sample obtained from a healthy subject (adapted from Vega et al., Sci Rep. 5: 7988 (2015).
Figure 11:
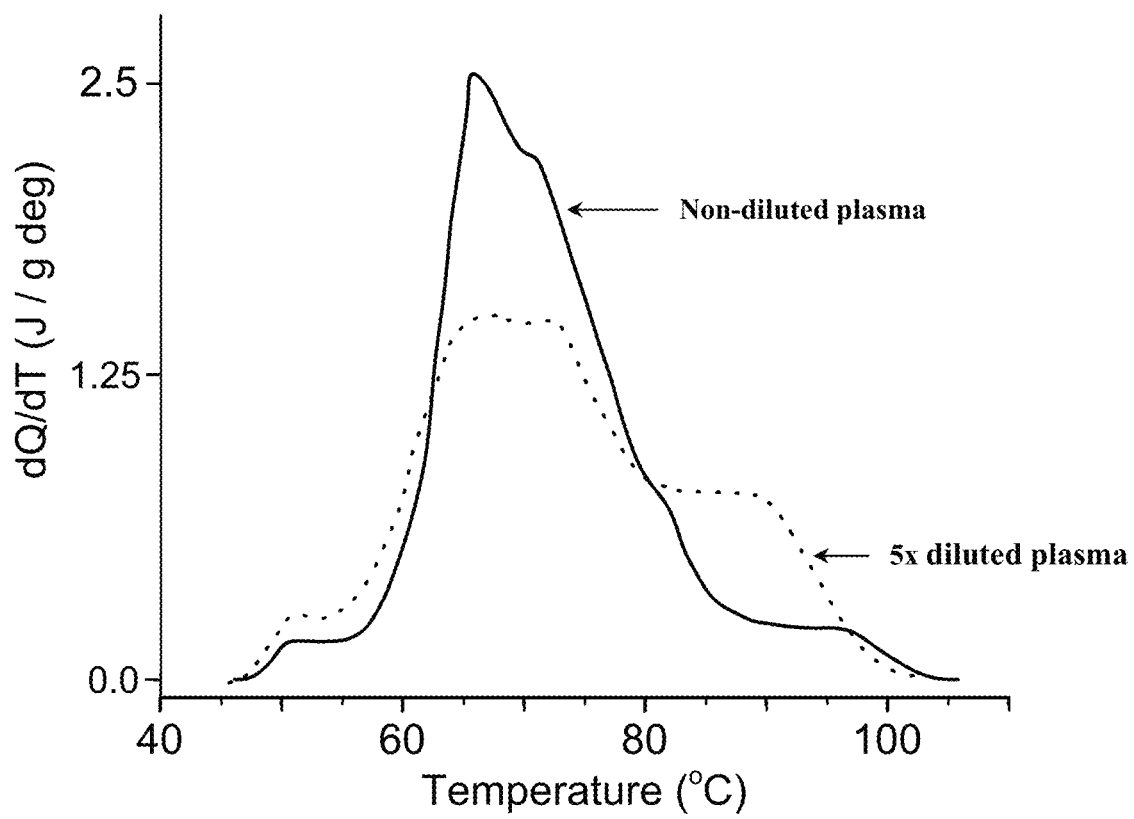
FIG. 11 shows heat absorption curves (heat capacity dQ/dT, J $g^{-1\circ}$ $C.^{-1}$) as a function of temperature of undiluted (solid line) and 5× diluted (dot line) plasma samples obtained from a patient suffering from myeloblastoma, using the device and methods disclosed herein.

The melting curve profiles obtained using non-diluted plasma/serum samples and the DSC device described herein significantly differ from those obtained using conventional DSC techniques that only employ diluted samples. Compare FIG. 7 with FIG. 6(*d*). First, the integral melting width (i.e., the (delta) $T_m$ at half max) is twice as wide in diluted plasma samples compared to undiluted samples. Particularly, the observed melting temperature of immunoglobulins (which play a critical role in the diagnosis of various cancers via DSC) is lower than expected when diluted plasma samples are used. Second, deconvolution analysis of diluted plasma samples reveals that the peak area of the albumin curve is merely 15%, which is significantly lower than the expected albumin concentration of 50% reported by clinical-biochemical data. In contrast, deconvolution analysis of undiluted samples as disclosed herein shows a peak area of about 50% for the albumin curve. Third, deconvolution analysis of diluted plasma samples shows a peak at 63° C., which may be an artifact of using diluted plasma solutions. Fourth, the heat capacity of melted plasma/serum proteins in diluted samples is significantly increased compared to that observed in undiluted samples. Fifth, the area of the 4th deconvolution peak at 70° C. (which corresponds to Y-globulin) is about 25% for diluted samples, which is higher than the expected Y-globulin concentration of 12-15% reported by clinical data. Further, FIG. 11 demonstrates that dilution of a plasma sample (e.g., by 5×) can significantly alter the peak intensity and shape of the DSC curve of a diseased patient (e.g., a patient suffering from myeloblastoma). Thus, the melt curves rendered using traditional DSC methods (diluted samples) are not an accurate reflection of the actual thermostability profiles of the plasma/serum proteins in vivo (i.e., undiluted).

Further, unlike DSC methods using diluted samples, the high resolution and sensitivity of the methods of the present technology permits reliable detection of the peak at around 58-60° C. in cancer patients. See FIG. 1.

These results demonstrate that the DSC methods of the present technology can effectively detect thermostable variants of proteins and/or metabolites present in small volume undiluted biological samples. Accordingly, the devices and methods of the present technology are useful in detecting breast cancer in subjects, and/or identifying subjects that are at-risk for developing breast cancer.

Example 3: Use of the DSC Device and Methods of the Present Technology to Detect Onset of Relapse and/or Monitor Disease Progression in Breast Cancer Patients This Example demonstrates that the DSC device and methods of the present technology are useful in detecting the onset of relapse and/or monitoring disease progression in patients diagnosed with breast cancer.

FIG. 3 shows the DSC melting curves of plasma/serum samples obtained from the 56 year old stage I breast cancer female patient described in FIG. 1 at 1-13 years after surgical operation. No significant changes in the melting profile of plasma/serum proteins were observed during the first eight years after surgery (compare solid line in FIG. 3 with dash line in FIG. 1). In contrast, the melting profile of plasma/serum proteins gradually changed between 9-10 years post-surgery (dot line). Specifically, the main fraction of albumin that melts at 62° C. in a healthy control subject, shifted to 64° C. and the melting curve gradually widened at its half high ($\Delta T_m$) from 8.5° C. to 10.5° C. A weak shoulder at 58-60° C. (dot line) also appeared, and became more prominently expressed at the end of 10 years (coincided with a clinical diagnosis of stage I breast cancer at the time). At 11-12 years post-surgery, the shoulder near 57-60° C. became more definite, and the $T_m$ and $\Delta T_m$ of the main albumin fraction increased by a few degrees (coincided with a clinical diagnosis of stage II breast cancer and lung metastases at the time). At 13-14 years post-surgery, the shoulder transformed into a clear peak with a maximum at 59° C.±1° C., and the $T_m$ of the main albumin fraction increased by 6° C. $T_m$ and $\Delta T_m$ of the main albumin fraction continued to increase, and reached 70±1° C. and 16±1.5° C., respectively at end of the 13th year (coincided with a clinical diagnosis of stage IV breast cancer and distant metastases in lungs and liver at the time).

Thus, the simultaneous appearance of a weak shoulder at 58-60° C. and the increase in $T_m$ and $\Delta T_m$ of albumin fatless fraction by 2-3° C. and 8.5-11° C. respectively (relative to that observed in healthy controls), signal the onset of breast cancer relapse. The increase in the $T_m$ and $\Delta T_m$ of the main albumin fraction by 2-3° C. and 8.5-12° C., respectively, without any significant changes in the integral curve profile may correlate with the early stages of inflammation.

Figure 4:
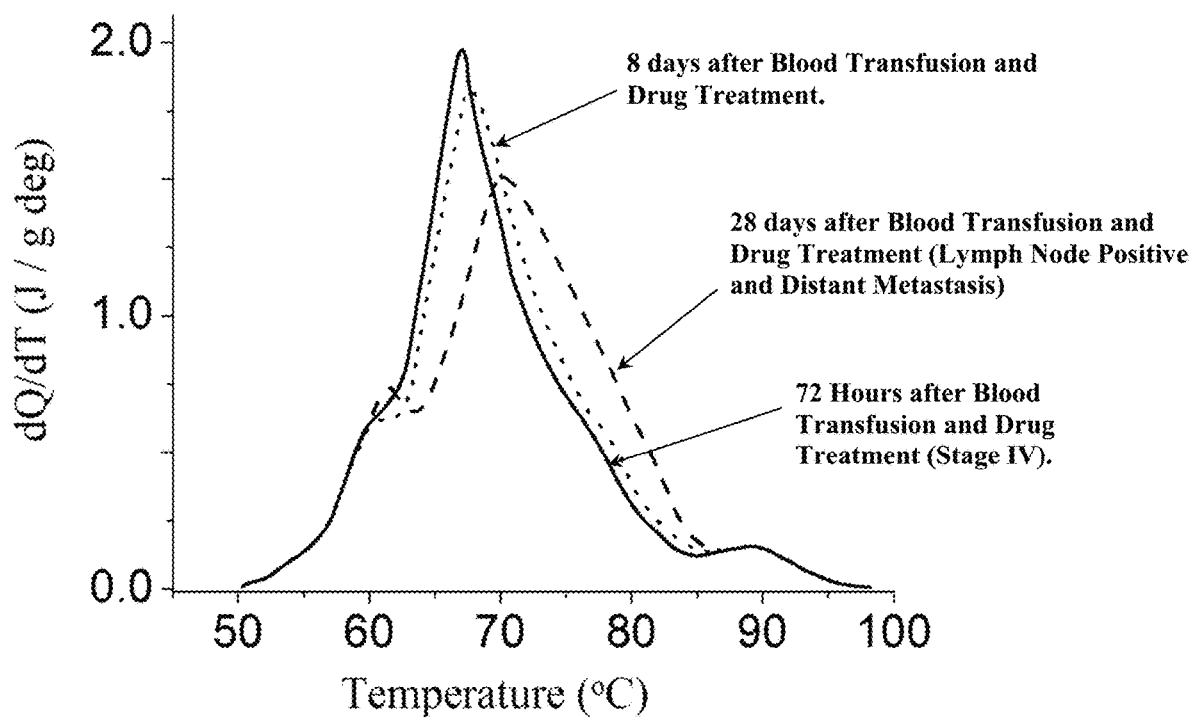
FIG. 4. shows heat absorption curves (heat capacity dQ/dT, J $g^{-1°}$ $C.^{-1}$) as a function of temperature of serum samples obtained from the same 56 year old female patient described in FIGS. 1 and 3 after treatment, recalculated per gram biomass: Solid line: 72 hours after blood transfusion and drug treatment (stage IV); Dot line: 8 days after blood transfusion and drug treatment; Dash line: 28 days after blood transfusion and drug treatment, clinical diagnosis revealed patient was lymph node positive with distant metastasis.

FIG. 4 shows the same stage IV breast cancer female patient (dot dash line in FIG. 3) after drug treatment. Drug treatment caused the DSC curve of plasma/serum proteins to shift towards the DSC profile of stage II breast cancer in about one week following drug administration. However, the DSC curve of the plasma/serum proteins gradually became similar to the DSC profile of stage IV breast cancer in about one or two months following drug administration.

These results demonstrate that the DSC methods of the present technology can effectively detect thermostable variants of proteins and/or metabolites present in small volume undiluted biological samples. Accordingly, the devices and methods of the present technology are useful in detecting the onset of relapse and/or monitoring disease progression in patients diagnosed with breast cancer.

Example 4: Use of the DSC Device and Methods of the Present Technology to Monitor Therapeutic Efficacy in Breast Cancer Patients This Example demonstrates that the DSC device and methods of the present technology are useful in monitoring the efficacy of a therapeutic regimen in breast cancer patients.

Figure 5:
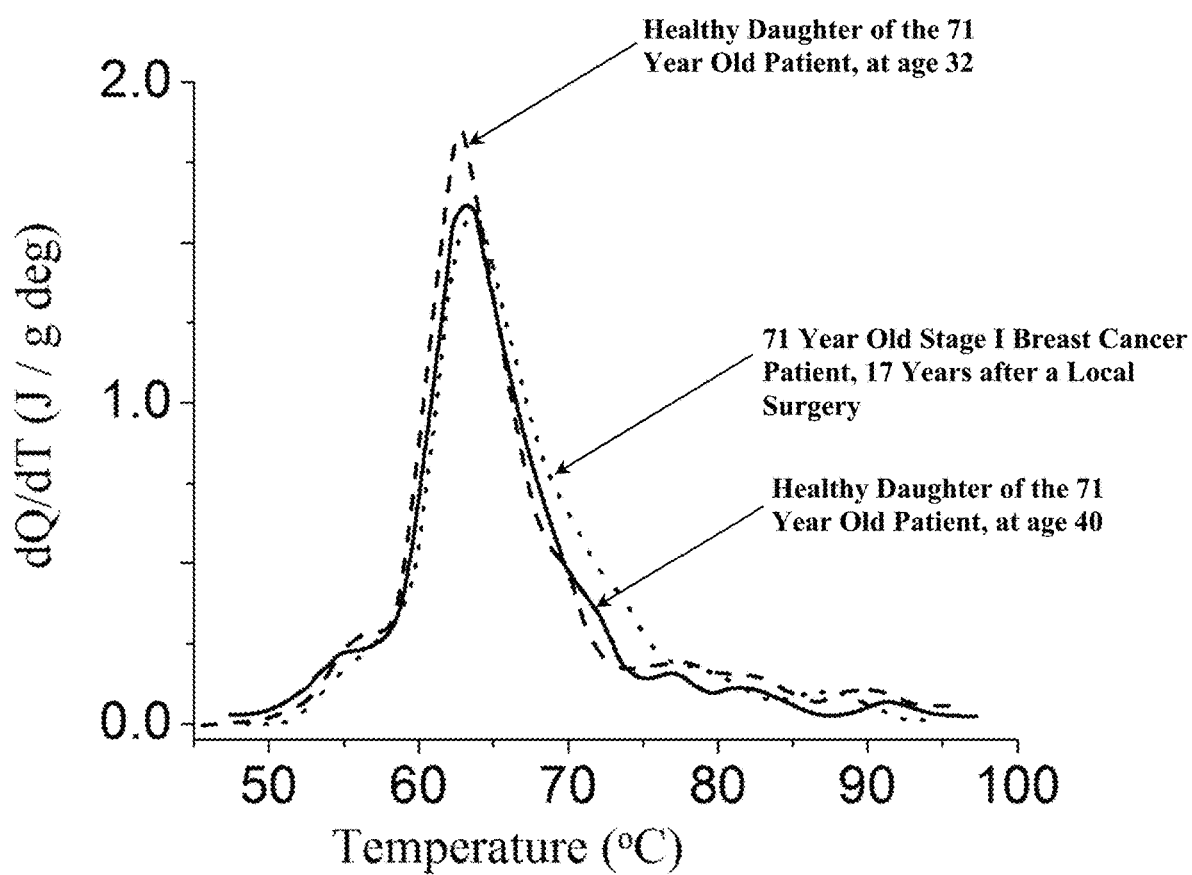
FIG. 5 shows heat absorption curves (heat capacity dQ/dT, J $g^{-1°}$ $C.^{-1}$) as a function of temperature of blood plasma samples obtained from female patients, recalculated per gram biomass: Dot line: 71 year old stage I breast cancer patient, 17 years after a local surgery. Dash and solid lines: a healthy daughter of the same 71 year old patient, at age 32 (dash line) and age 40 (solid line).

FIG. 5 shows the DSC melting curves of plasma/serum samples obtained from a breast cancer patient (group 2) 17 years after she received a local lumpectomy in combination with radiation therapy, and her healthy daughter at age 32 and 40. The tumor tissue size was 10 mm (in 1998, diagnosis was stage I breast cancer with lymph node metastasis). The patient did not receive a course of chemotherapy in the 17 years following the lumpectomy procedure. As shown in FIG. 5, the peak intensity (DC'=dQ/dT=1.6 J/g deg) and shape of the DSC curve of the treated breast cancer patient resembled that observed in the healthy daughter, thereby demonstrating the efficacy of the therapeutic regimen in the breast cancer patient.

These results demonstrate that the DSC methods of the present technology can effectively detect thermostable variants of proteins and/or metabolites present in small volume undiluted biological samples. Accordingly, the devices and methods of the present technology are useful in monitoring the efficacy of a therapeutic regimen in a patient in need thereof.

Example 5: Use of the DSC Device and Methods of the Present Technology to Detect Disease or Infection This Example demonstrates that the DSC device and methods of the present technology are useful in detecting a disease or condition in a subject.

Table 1 provides the thermostability signatures of different diseases using the DSC device and methods of the present technology. Undiluted plasma samples were used in every instance.

TABLE 1

Figure 12:
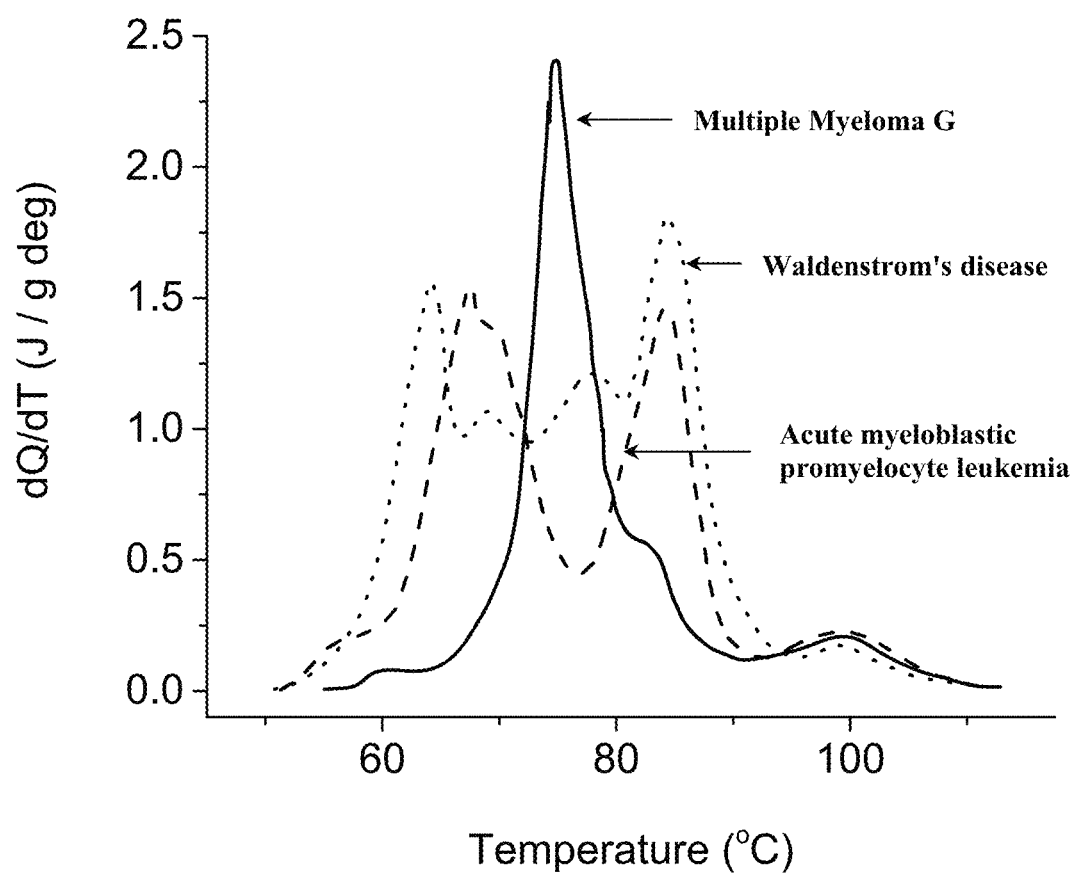
FIG. 12 shows heat absorption curves (heat capacity dQ/dT, J $g^{-1\circ}$ $C.^{-1}$) as a function of temperature of whole blood samples obtained from a patient suffering from multiple myeloma G (solid line); acute myeloblastic promyelocyte leukemia (dash line); and Waldenstrom's disease (dot line).

| Disease or Condition | Thermostability Signatures Generated with the DSC Device of the Present Technology |
|---|---|
| Normal Healthy Control | Main Max Corresponds to Albumin peaks at 61.5° C. ± 1° C.<br>Main Peak $\Delta T_m$ at half height of max. 7.5-10° C.<br>dQ/dT ($\Delta C$ excess) = 1.35-1.75 j/g deg<br>Shoulder at 70° C. corresponds to melting of Y-Globulin; $\Delta C$ excess = 0.45 j/g deg<br>Peaks at 55° C., 78° C., 80° C. and 92° C. correspond to Fibrinogen (2 peaks) at 55 and 92° C.; protein inhibitors at 78° C.; fatty fraction of Albumin at 80° C.<br>Y-globulin - $\Delta T_m$ after deconvolution about 8°; $\Delta C$ excess = 0.4 ± 0.1 j/g deg; Melting temperature about 70°;<br>Total protein concentration: 55% Albumins, 15% Y-globulins, 3% Fibrinogen and other. |
| Brain Cancer (myoblastoma) | Appearance of new shoulders at 69° C. and 75° C.;<br>$\Delta T_m$ of Dual Peak on half height increased by 200-300%<br>Reduction in $\Delta C$ excess (dQ/dT) by 50% |
| Hepatitis C | Main Max splits into two peaks: 67° C. and 70° C.<br>$\Delta T_m$ at half height of max. increased by 100-200%;<br>Reduction in excess heat capacity (dQ/dT) by 12-45% and 22-60% for peaks 67° C. and 70° C. compared to dQ/dT of Albumin;<br>New weak shoulder appears on 84° C. (See FIG. 9(a)) |
| Breast Ductal carcinoma. Risk Factor | New weak shoulder appears at about 59° C.<br>Main maximum shifts to higher temperatures by 3° C.<br>dQ/dT ($\Delta C$ excess) reduced by 10-20%<br>$\Delta T_m$ - increased by 30%<br>Y-globulin concentration increased by around 40%<br>$\Delta T_m$ Y-globulin after deconvolution = 8° C;<br>$T_m$ Y-globulin after deconvolution = 72° C. |
| Breast Ductal carcinoma. Stage (III-IV) | Weak shoulder transforms to a sharp individual peak around 60° C.<br>Width after deconvolution = 2.5 ± 0.5° C.<br>Main peak shifts towards high temperature by 6-7° C.;<br>Main Peak width increased by 250-300%<br>$T_m$ Y-globulin after deconvolution - 75° C.; |
| Multiple Myeloma G (G1; G2 isoforms) | 400-500% increase in Y-Globulin concentration<br>Sharp peak at 70, 75, 82 ± 1.3° C.<br>$\Delta C$ excess of Y-Globulin- increased by about 400%<br>20-35% decrease in $\Delta C$ excess of Albumin<br>Main Peak width increased by 250-300% (See FIG. 12) |

TABLE 1-continued

Figure 10:
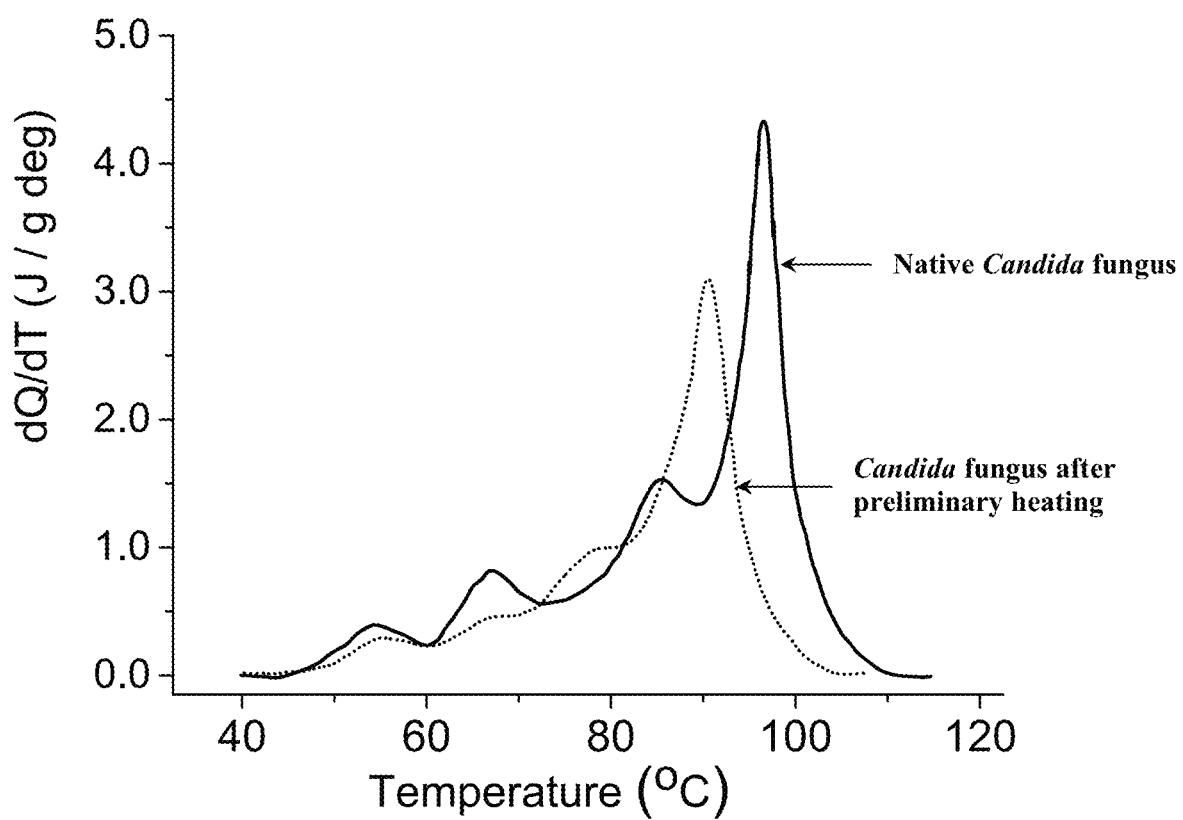
FIG. 10 shows heat absorption curves (heat capacity dQ/dT, J $g^{-1\circ}$ $C.^{-1}$) as a function of temperature of a Candida fungal suspension harvested from the infected tissue of a breast cancer patient. Dry mass 2.6 mg, vessel volume 0.2 mL.

| Disease or Condition | Thermostability Signatures Generated with the DSC Device of the Present Technology |
|---|---|
| Multiple Myeloma A | 400-500% increase of Y-Globulin concentration<br>Sharp peak at 70 ± 1.0° C.<br>ΔC excess of Y-Globulin - increased by about 400%<br>20-35% decrease in ΔC excess of Albumin<br>Main Peak width increased by 60-70% |
| Bence Jones Myeloma | $\Delta T_m$ at half height of max 11-12° C. (10-12% more than high norm);<br>Integral Curve ΔC excess = 0.9-0.11 j/g deg<br>Bence Jones protein concentration increased by 200-250%;<br>Albumin Concentration decreased by 15-20%.<br>Appearance of new peak at 57 ± 1.3° C. (marker); ΔC excess of New Peak 0.45-0.55 j/g deg (without deconvolution);<br>$\Delta T_m$ of New Peak 3 ± 0.5° C. |
| Candida | Native<br>Appearance of three new peaks at 55° C., 67° C., 85.5° C., corresponding ΔC excess: 0.4, 0.85, 1.6 j/g/deg;<br>Fungal Chromatin $T_m$ = 97° C.; ΔC excess: 4.5 j/g/deg;<br>ΔT = 6.1° C.<br>After Heating at 110° C.<br>Appearance of three new peaks at 55° C., 67° C., 78° C., corresponding ΔC excess: 0.3, 0.5, 1.0 j/g/deg<br>Fungal Chromatin $T_m$ = 91° C.; ΔC excess 3.1 j/g/deg;<br>ΔT = 9.5° C. (See FIG. 10) |
| Myeloblastoma (undiluted) | Appearance of new shoulders or peaks at 51.5° C., 66.0° C., 71.5° C., 80.1° C., 90-105° C. (wide), corresponding ΔC excess = 0.16, 2.5, 2.18, 0.66, 0.18 j/g/deg;<br>ΔT Integral peak = 14.8° C. (FIG. 11) |
| Myeloblastoma (diluted) | Appearance of new shoulders or peaks at 51.5° C., 66.0° C. (wide), 74° C. (wide), 80° C.-100° C. (wide), corresponding ΔC excess = 0.24, 1.36, 1.35, 0.66 j/g/deg<br>ΔT Integral peak = 30° C. (FIG. 11) |
| Acute myeloblastic promyelocyte leukemia | Appearance of new shoulders or peaks at 62° C., 66° C. (corresponds to Albumin), and 85° C. Hemoglobin;<br>ΔC excess for Hemoglobin around 7° C. (See FIG. 12) |
| Waldenstrom's disease | Power peak at 66° C. comprises albumin and other proteins (See FIG. 12) |

Figure 9A:
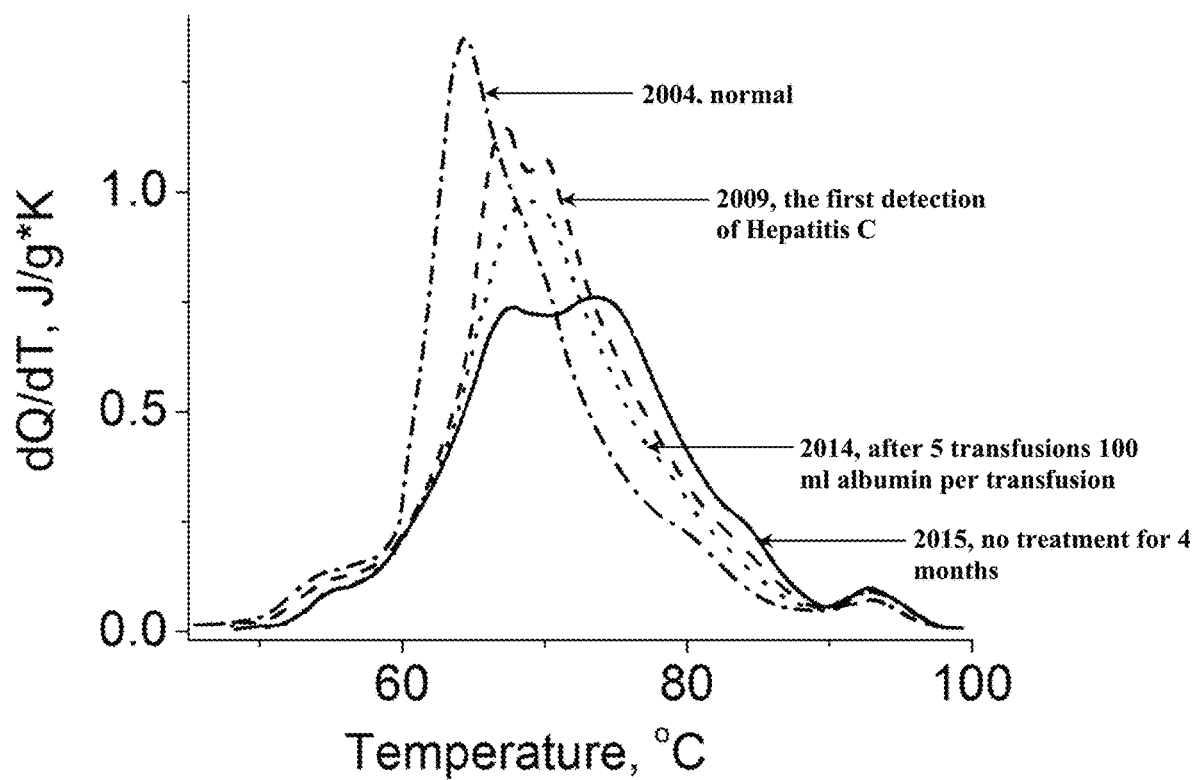
FIG. 9(a) shows heat absorption curves (heat capacity dQ/dT, J $g^{-1\circ}$ $C.^{-1}$) as a function of temperature of blood plasma samples obtained from a Hepatitis C-infected patient.
Figure 9B:
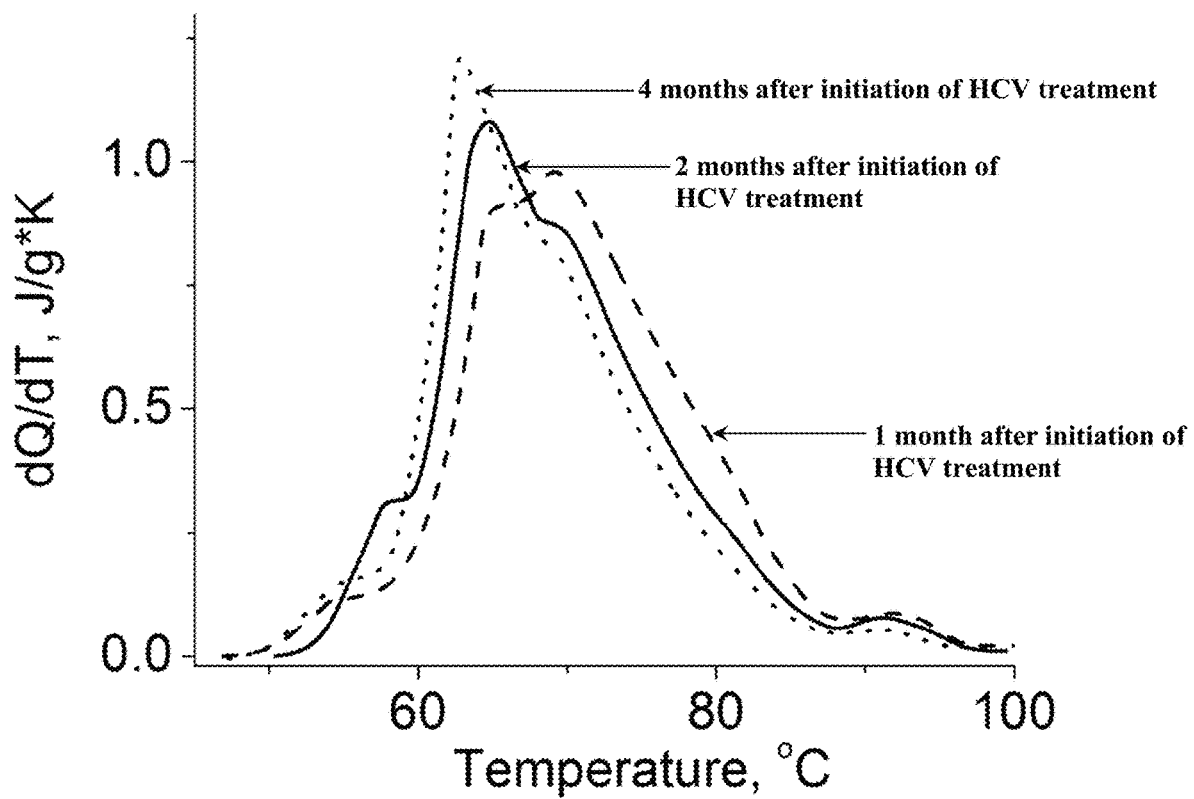
FIG. 9(b) shows the DSC curves of plasma samples obtained from a 65 year old female patient after initiation of Hepatitis C treatment.

FIG. 9(a) shows that the presence of a double peak at 67° C. and 70° C. is an indicator of Hepatitis C infection. Further, the DSC curve of the Hepatitis C-infected patient showed a 100-200% increase in $\Delta T_m$ at half max, significant reduction in excess heat capacity (dQ/dT) for peaks 67° C. and 70° C. compared to dQ/dT of Albumin, and a 5.5-8.5° C. increase in $T_m$. FIG. 9(a) also shows that treatment of the Hepatitis C infection caused the DSC curve of the Hepatitis C-infected patient to coalesce to a single peak. However, a double peak at 67° C. and 74° C. appeared when treatment was suspended for four months and was accompanied by a two-fold decrease in dQ/dT. FIG. 9(b) shows the DSC curves of plasma samples obtained from a 65 year old female patient that began HCV treatment. As shown in FIG. 9(b), the peak intensity and shape of the DSC curve of the HCV-infected patient after 4 months treatment resembled that observed in a normal patient (see dash dot line in FIG. 9(a)), thereby demonstrating the efficacy of the therapeutic regimen in the HCV-infected patient.

These results demonstrate that the DSC methods of the present technology can effectively detect thermostable variants of proteins and/or metabolites present in small volume undiluted biological samples. Accordingly, the devices and methods of the present technology are useful in detecting a disease or infection in a subject and/or monitoring the efficacy of a therapeutic regimen in a patient in need thereof.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least,"

"greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

The invention claimed is:

1. A method for detecting thermostable variants of proteins and/or metabolites in a biological sample comprising:
    (a) loading an unprocessed fraction of the biological sample into a vessel of a differential scanning calorimeter, wherein the differential scanning calorimeter comprises a test channel comprising a wall forming a receiving end that slopes at a predetermined angle, and wherein the vessel of the differential scanning calorimeter has a sloping outer wall and is configured to slide into the test channel and mate with the receiving end of the test channel;
    (b) sliding the vessel of the differential scanning calorimeter into the test channel such that an entirety of the sloping outer wall of the vessel contacts the wall of the receiving end of the test channel, wherein the contact between the entirety of the sloping outer wall of the vessel and the wall of the receiving end of the test channel is configured to promote direct heat transfer between the vessel and the test channel;
    (c) heating continuously the biological sample in the vessel throughout a scan;
    (d) generating a signature DSC thermogram from the unprocessed fraction of the biological sample after the scan; and
    (e) detecting thermostable variants of proteins and/or metabolites when at least one alteration is present in the signature DSC thermogram of the unprocessed fraction of the biological sample relative to a DSC thermogram generated from a normal control sample.

2. The method of claim 1, wherein the wall of the vessel slopes at the predetermined angle.

3. The method of claim 1, wherein the predetermined angle is between about 1° and about 5°.

4. The method of claim 1, wherein the unprocessed fraction of the biological sample is plasma, serum, whole blood, or tissue.

5. The method of claim 1, wherein the biological sample is obtained from a patient that is at risk for or is suspected of having cancer.

6. The method of claim 5, wherein the cancer is breast cancer, brain cancer, acute myeloblastic promyelocyte leukemia, Waldenstrom's disease, or myeloma.

7. The method of claim 5, wherein the patient lacks any detectable rigid tumor mass.

8. The method of claim 5, wherein the patient is suffering from stage 0, stage I, stage II, stage III, or stage IV cancer.

9. The method of claim 1, wherein the biological sample is obtained from a patient that is suffering from a disease or condition.

10. A method for detecting the onset of relapse in a patient diagnosed as having a disease or condition comprising:
    (a) loading an unprocessed fraction of a biological sample obtained from the patient into a vessel of a differential scanning calorimeter, wherein the differential scanning calorimeter comprises a test channel comprising a wall forming a receiving end that slopes at a predetermined angle, and wherein the vessel of the differential scanning calorimeter has a sloping outer wall and is configured to slide into the test channel and mate with the receiving end of the test channel;
    (b) sliding the vessel of the differential scanning calorimeter into the test channel such that an entirety of the sloping outer wall of the vessel contacts the wall of the receiving end of the test channel, wherein the contact between the entirety of the sloping outer wall of the vessel and the wall of the receiving end of the test channel is configured to promote direct heat transfer between the vessel and the test channel;
    (c) heating continuously the biological sample in the vessel throughout a scan;
    (d) generating a signature DSC thermogram from the unprocessed fraction of the biological sample after the scan; and
    (e) detecting the onset of relapse in the patient when at least one alteration is present in the signature DSC thermogram of the unprocessed fraction of the biological sample relative to a DSC thermogram generated from a normal control sample, wherein the at least one alteration is similar or identical to that observed in a DSC thermogram generated from a positive control sample having the disease or condition.

11. The method of claim 10, wherein the disease or condition is cancer, a pathogenic infection, diabetes mellitus, cardiovascular disease, neurodegenerative disease, or rheumatic disease.

12. The method of claim 11, wherein the cancer is breast cancer, brain cancer, acute myeloblastic promyelocyte leukemia, Waldenstrom's disease, or myeloma.

13. The method of claim 10, wherein the patient lacks any detectable rigid tumor mass.

14. The method of claim 11, wherein the neurodegenerative disease is Alzheimer's disease, Amyotrophic lateral sclerosis, Friedreich's ataxia, Huntington's disease, Lewy body disease, Parkinson's disease, or spinal muscular atrophy.

15. The method of claim 11, wherein the disease is the rheumatic disease selected from the group consisting of: osteoarthritis, rheumatoid arthritis, ankylosing spondylitis, Sjögren's syndrome, Antinuclear Antibodies (ANA), Antiphospholipid Syndrome, Calcium Pyrophosphate Deposition (CPPD), Carpal Tunnel Syndrome, Cryopyrin-Associated Autoinflammatory Syndrome (CAPS), Dermatomyositis, familial Mediterranean fever, fibromyalgia, giant cell arteritis, glucocorticoid-induced osteoporosis, gout, granulomatosis with Polyangitis (Wegener's), hypermobility, Hyperimmunoglobulin D Syndrome, inflammatory myopathies, juvenile arthritis, scleroderma, Lyme disease, metabolic myopathies, osteonecrosis, osteonecrosis of the jaw (ONJ), osteoporosis, Paget's disease, PFAPA (Periodic Fever, Aphthous Stomatitis, Pharyngitis, Adenitis Syndrome), polymyalgia rheumatic, psoriatic arthritis, Raynaud's phenomenon, reactive arthritis, spinal stenosis, spondyloarthritis, Systemic Lupus Erythematosus, Takayasu's arteritis, Tendinitis & bursitis, Tumor Necrosis Factor Receptor Associated Periodic Syndrome, and vasculitis.

16. The method of claim 11, wherein the disease is the pathogenic infection selected from the group consisting of: a bacterial infection, a viral infection or a fungal infection.

17. The method of claim 16, the pathogenic infection is caused by Clostridium difficile, carbapenem-resistant Enterobacteriaceae, multidrug resistant *Acinetobacter*, multidrug resistant *Campylobacter*, flucoazole resistant *Candida*, extended spectrum beta-lactamase-producing Enterobacteriaceae, Vancomycin Resistant Enterococci, Multidrug resistant *Pseudomonas aeruginosa*, drug resistant Non-typhoidal *Salmonella*, drug resistant *Salmonella* serotype *Typhi*, drug resistant *Shigella*, Methicillin-Resistant *Staphylococcus aureus*, drug resistant *Streptococcus pneumoniae*, drug resistant *Mycobacterium tuberculosis*, hepatitis B virus, hepatitis C virus, HIV, Human Papilloma Virus, or Epstein Barr virus.

18. The method of claim 10, wherein the unprocessed fraction of the biological sample is plasma, serum, whole blood, or tissue.

* * * * *